(12) United States Patent
Matusch

(10) Patent No.: US 10,022,500 B2
(45) Date of Patent: Jul. 17, 2018

(54) DUAL-CHAMBER CYLINDER-PISTON UNIT FOR THE LYOPHILISATION, STORAGE, RECONSTITUTION AND APPLICATION OF INJECTION SOLUTIONS FOR AN INJECTOR, AND METHOD FOR FILLING THE CYLINDER-PISTON UNIT

(71) Applicant: Rudolf Matusch, Marburg (DE)

(72) Inventor: Rudolf Matusch, Marburg (DE)

(73) Assignee: LTS LOHMANN THERAPIE—SYSTEME AG, Andernach (DE)

( * ) Notice: Subject to any disclaimer, the term of this patent is extended or adjusted under 35 U.S.C. 154(b) by 329 days.

(21) Appl. No.: 14/941,858

(22) Filed: Nov. 16, 2015

(65) Prior Publication Data

US 2016/0067405 A1    Mar. 10, 2016

Related U.S. Application Data

(60) Division of application No. 13/304,530, filed on Nov. 25, 2011, now Pat. No. 9,238,109, which is a
(Continued)

(30) Foreign Application Priority Data

May 29, 2009  (DE) .......................... 10 2009 023 335
Nov. 18, 2009  (DE) .......................... 10 2009 053 729

(51) Int. Cl.
*A61M 5/178*    (2006.01)
*A61M 5/315*    (2006.01)
(Continued)

(52) U.S. Cl.
CPC ............ *A61M 5/1782* (2013.01); *A61M 5/30* (2013.01); *A61M 5/3129* (2013.01);
(Continued)

(58) Field of Classification Search
CPC .... A61M 5/1782; A61M 5/30; A61M 5/3129; A61M 5/31596; A61M 2005/3118; A61M 5/3007; B65B 3/003
See application file for complete search history.

(56) References Cited

U.S. PATENT DOCUMENTS 5,626,567 A    5/1997 Gmeiner
2004/0097874 A1    5/2004 Griffiths et al.
(Continued)

FOREIGN PATENT DOCUMENTS

EP    0 511 183 A1    10/1992
FR    2 082 128 A5    12/1971
(Continued)

*Primary Examiner* — Theodore Stigell
(74) *Attorney, Agent, or Firm* — Ronald S. Lombard

(57) ABSTRACT

A method for filling a cylinder/piston unit (1) for a needle-free injector comprising a chamber (3) arranged in a cylinder (2), for receiving an injection solution (4), a front wall (5) having at least one nozzle borehole or an outlet element (6), and a second piston (7) arranged to move in the chamber. The chamber (3) is made in two parts with a first chamber (8) and a concentric second chamber (9) having a smaller cross section than the first chamber. A first piston (10) closes the first chamber (8) and the second piston closes the second chamber (9). The second piston comprises at least one flow channel (16) or the first chamber comprises at least one closable, axially oriented freeze-drying channel (34), and the second chamber (9) comprises at least one axially oriented flow channel (36), on the respective rear ends of the chambers (8, 9).

3 Claims, 27 Drawing Sheets

Related U.S. Application Data continuation-in-part of application No. PCT/EP2010/002974, filed on May 14, 2010.

(51) Int. Cl.
*A61M 5/31* (2006.01)
*B65B 3/00* (2006.01)
*A61M 5/30* (2006.01)

(52) U.S. Cl.
CPC ......... *A61M 5/31596* (2013.01); *B65B 3/003* (2013.01); *A61M 5/3007* (2013.01); *A61M 2005/3118* (2013.01)

(56) References Cited

U.S. PATENT DOCUMENTS

| | | |
|---|---|---|
| 2008/0146997 A1 | 6/2008 | Hoffmann |
| 2008/0287885 A1 | 11/2008 | Hoffmann et al. |
| 2009/0159553 A1 | 6/2009 | Hoffmann et al. |
| 2009/0166978 A1 | 7/2009 | Hoffmann et al. |
| 2009/0254036 A1 | 10/2009 | Asmussen |
| 2009/0281496 A1 | 11/2009 | Matusch |

FOREIGN PATENT DOCUMENTS

| | | | |
|---|---|---|---|
| FR | 2 613 628 A1 | 4/1987 | |
| WO | WO 2004/026376 A1 | 4/2004 | |
| WO | WO 2007/034020 A1 | 3/2007 | |
| WO | WO 2007034020 A1 * | 3/2007 | ............ A61M 5/284 |

* cited by examiner

DUAL-CHAMBER CYLINDER-PISTON UNIT FOR THE LYOPHILISATION, STORAGE, RECONSTITUTION AND APPLICATION OF INJECTION SOLUTIONS FOR AN INJECTOR, AND METHOD FOR FILLING THE CYLINDER-PISTON UNIT

CROSS-REFERENCE TO RELATED APPLICATION

This is a divisional and claims the benefit of U.S. patent application Ser. No. 13/304,530 filed Nov. 25, 2011, which issued as U.S. Pat. No. 9,238,109 B2 on Jan. 19, 2016. The said U.S. patent application Ser. No. 13/304,530 is a continuation-in-part application of pending international application PCT/EP2010/002974 filed May 14, 2010 and claiming the priority of German Application No. 10 2009 023 335.0 filed May 29, 2009 and claiming the priority of German Application No. 10 2009 053 729.5 filed Nov. 18, 2009. The said U.S. patent application Ser. No. 13/304,530, the said pending international application PCT/EP2010/002974, the said German Application No. 10 2009 023 335.0, and the said German Application No. 10 2009 053 729.5 are all incorporated herein by reference in their entirety.

BACKGROUND OF THE INVENTION

The invention relates to a cylinder-piston unit for a needle-free injector, with a chamber which is arranged in a cylinder and is intended for receiving an injection solution, an end wall with at least one nozzle bore or an outlet element, and pistons arranged movably in the chamber. The invention furthermore relates to a method for correspondingly filling the cylinder-piston unit.

Cylinder-piston units are inserted into injectors which are known, for example, from US 2008/014997 A1, DE 10 2007 004 211 A1 or DE 10 2007 008 369 A1.

Liquid drugs are understood by injection solution. The specialized terms used will be explained in more detail below. The term drugs is known to a person skilled in the art. These include substances or mixtures of substances for human or animal medicine. They comprise the pharmaceutical active compound or active compounds and further customary components rendering said active compound pharmaceutically usable, in particular water.

DE 10 2005 054 600 A1 discloses a cylinder-piston unit with a cylinder and a piston which is guided therein, wherein the cylinder and the piston enclose a chamber which is at least temporarily fillable with active compound, and the cylinder has at least one outlet element at its front end. The cross section of the chamber or the cross section of the inner wall of the cylinder increases at least in areas from the front to the rear. At least in the front region—which faces the outlet element—the piston has a front, elastic skirt, the front outer edge of which, when the piston is unloaded, spans a cross-sectional area which is larger than an area spanned by a contour lying in the region of the transition from the skirt to the skirt-bearing piston section.

DE 10 2006 040 888 B3 discloses a closure system for containers for storing or administering liquid, pasty or powdery substances, said closure system comprising a cap provided with a passage hole, and a closure element. In this case, the cap holds the closure element in a frictional and/or form-fitting manner on the container in the region of the opening to be closed by means of a latching element present on the container. The end surface which surrounds the container opening and on which the closure element rests has a depression. The closure element is a virus-proof, bacteria-proof and spore-proof film which lies on the end surface and, at least in areas, over the depression. When the cap is placed on, an elastomer or adhesive ring which fills the depression is arranged between the closure element and the depression.

DE 10 2006 045 959 B3 discloses a cylinder-piston unit with a cylinder and a piston which is guided therein and is sealed by rubber in a sterile manner, wherein the cylinder and the piston enclose a chamber which is at least temporarily fillable with active compound, and the front end of the cylinder has at least one outlet element. The piston which is at rest in a rear position is sealed in a sterile manner in relation to the cylinder by a static rear sealing element, wherein, in a sealing position, the two sealing elements bear in each case on the cylinder wall and on the piston wall. A parking space receiving the respective sealing element is arranged spatially behind each static sealing element. When the piston is actuated, the individual static sealing elements are transferred from their respective sealing position into a parking position located in the parking space, wherein, in the parking position, each sealing element makes contact either only with the cylinder wall or only with the piston wall. At least one dynamic sealing element which is on the piston side and, at least when the piston is actuated, bears against the inner wall of the cylinder is arranged between the two static sealing elements.

In the known embodiments, the cylinder-piston unit is filled with the injection solution either directly prior to use by the user of the disposable injector or the injection solution is placed into the cylinder-piston unit at the manufacturing factory and it is then also stored in the cylinder-piston unit. A finished injection solution is therefore present in the cylinder-piston unit for the duration of the possible storage time. One possible, preferred manner of storing an active compound involves freeze-drying (lyophilizing) the active compound solution and storing the active compound in the form of a powder. A lyophilizate of this type has a longer shelf life than in dissolved form. In order to obtain a finished injection solution prior to the injection, the lyophilized active compound is dissolved in a solvent, such as water. An injectable solution is subsequently present.

Proceeding from said prior art, the invention is based on the object of specifying a cylinder-piston unit for receiving an injection solution and a method for filling the cylinder-piston unit, in which the injection solution is produced from a first drug component and a second drug component and is mixed to be ready or is dissolved only shortly prior to use. The further task is to design a cylinder-piston unit into which an injection solution which is to be freeze-dried can be placed in a sterile manner, said solution can then be freeze-dried and subsequently closed in an airtight and sterile manner. The solvent for the lyophilizate has to be stored adjacent thereto in such a manner that, in the event of use, said solvent can dissolve the lyophilizate to form an injection solution ready for use. Prior to application, said solution has to be located in a manner free from gas bubbles in a cylinder which is temporarily stable at up to 300 bar and has a nozzle which is to be released in a sterile manner and from which said solution can be shot under high pressure and without a needle through the skin into, for example, the subcutaneous fatty tissue.

SUMMARY OF THE INVENTION

These objects are achieved by a cylinder-piston unit according to the present invention and a corresponding method for filling the cylinder-piston unit. According thereto, the cylinder-piston unit, referred to, is characterized in that the chamber is of two-part design with a first chamber and a concentric second chamber, the cross section of the first chamber being larger than the cross section of the second chamber, in that the second chamber is formed such that it is closed by the second piston, and the first chamber is formed such that it is closed by a first piston, the first chamber being separated from the second chamber, and in that the second piston is formed with at least one closable transfer passage, or in that the first chamber is formed with at least one closable, axially aligned freeze-drying passage and the second chamber is designed with at least one axially aligned transfer passage, at the rear ends in each case of the chambers.

The arrangement of the second piston between the second chamber and the first chamber enables a first drug component to be separated from a second drug component. By the first and second pistons preferably being configured to have a respective piston body and an outer piston ring, different materials can be taken into consideration for the pistons. Both the outer piston ring of the first piston and that of the second piston are pressed, for example, upon insertion into the first chamber in such a manner that a passage or a flow edge is produced, through which the displaced air can escape in an unpressurized manner from the first chamber.

For the injecting, the inner piston bodies are pushed via a piston rod, for example by a prestressed spring, into the second chamber within a very short period of time in order to eject the injection solution under high pressure out of the nozzle(s) counter to a resistance—skin.

A preferred configuration provides forming the inner piston body, which is closest to the nozzle(s), with at least one sealing lip in order to improve the guidance and tightness between the inner piston body and the wall of the second chamber and/or to increase said guidance and tightness in a pressure-dependent manner.

The object mentioned above is furthermore achieved by the method, taking into consideration the cylinder-piston unit just described.

The method comprises at least the following steps:

filling a second chamber with a first drug component of an injection solution, wherein the volume of the first drug component is smaller than the volume of the second chamber;

inserting a second piston, which is compressed and allows the air to escape, into a first chamber until it makes contact with an annular surface in order to close the second chamber, the second chamber containing a gas cushion;

filling the first chamber above the second piston with a solvent, for example water, or with a second drug component, inserting a first compressed piston into the first chamber and closing the first chamber, pushing in the first piston, with nozzle(s) pointing upward in order to produce the injection solution from the lyophilizate or the first drug component, and the solvent or the second drug component by means of a piston slide, wherein, by causing positive pressure in the first chamber, a second inner piston body is pushed in a second outer piston ring in the direction of a second chamber until a previously closed transfer passage connects the second chamber to the first chamber and the solvent or the second component entirely enters the second chamber and is dissolved or mixed with the lyophilizate or the first drug component to provide the finished injection solution;

subsequently pushing in a first inner piston body together with the second inner piston body with the aid of the piston slide, by screwing the piston slide into a thread, partial thread or latching element, and squeezing a gas bubble out of the cylinder-piston unit, wherein the gas bubble is displaced out of the second chamber through (an) upwardly pointing nozzle bore(s) or outlet element(s) and a membrane which is fastened to the outer cylinder or to the closure cap and lifts off from the nozzle bore(s) or outlet element(s) when the gas cushion emerges, and closing the nozzle bore(s) or the outlet element(s) again in a sterile manner (pressure control valve) after the gas cushion emerges.

As a rule, the finished injection solution is metered in a sterile manner into the second chamber which is closed by the closure cap and membrane.

In a first embodiment, the second piston with the piston ring which has an upwardly closed passage which functions simultaneously as an overflow passage and freeze-drying passage (functions may also be positioned separately at different points on the piston ring) is fitted in such a manner that the entire gas space above the injection solution is in contact with the outside. In a second embodiment, the second piston with the piston ring is fitted in such a manner that the entire gas space above the injection solution is in contact with the outside by means of at least one axially aligned freeze-drying passage in the first chamber. Freeze-drying is then carried out. After the lyophilizing, the second piston with the piston ring is advanced as far as the annular surface such that the lyophilizate is sealed in a manner protected against moisture and oxygen. The solvent (for example water) is subsequently placed in a sterile manner into the first chamber and sealed by the first piston, for example by a compressed piston ring, without pressure being exerted on the solvent.

A preferred embodiment provides for the active compound of the injection solution to be freeze-dried in the second chamber.

BRIEF DESCRIPTION OF THE DRAWINGS

Further features and details of the invention emerge from exemplary embodiments of the invention that are illustrated in the following schematic drawings, in which.

DETAILED DESCRIPTION OF THE PARTICULAR EMBODIMENTS

In the description below of the exemplary embodiments, the front end of the cylinder-piston unit means the end closest to the surface of a patient. The rear end of the cylinder-piston unit is the end which is remote from the surface of the patient when the unit is used.

In all of the figures, identical technical elements are referred to by identical reference numbers.

Figure 1:
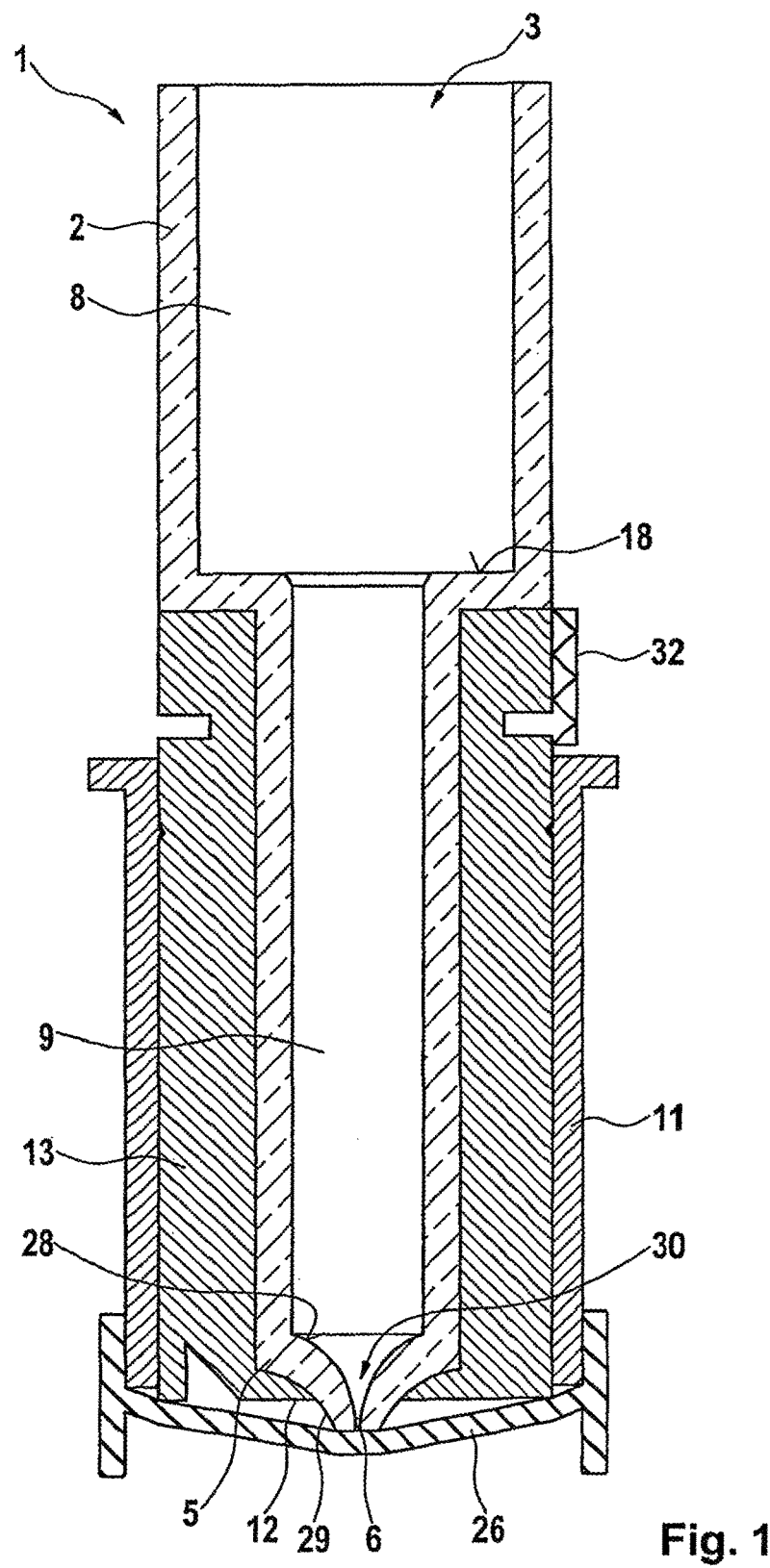
FIG. 1 shows a sectioned side view of a cylinder with two diameters and a pressure-stable outer cylinder of a cylinder-piston unit with a membrane fitted on a closure cap.
Figure 2:
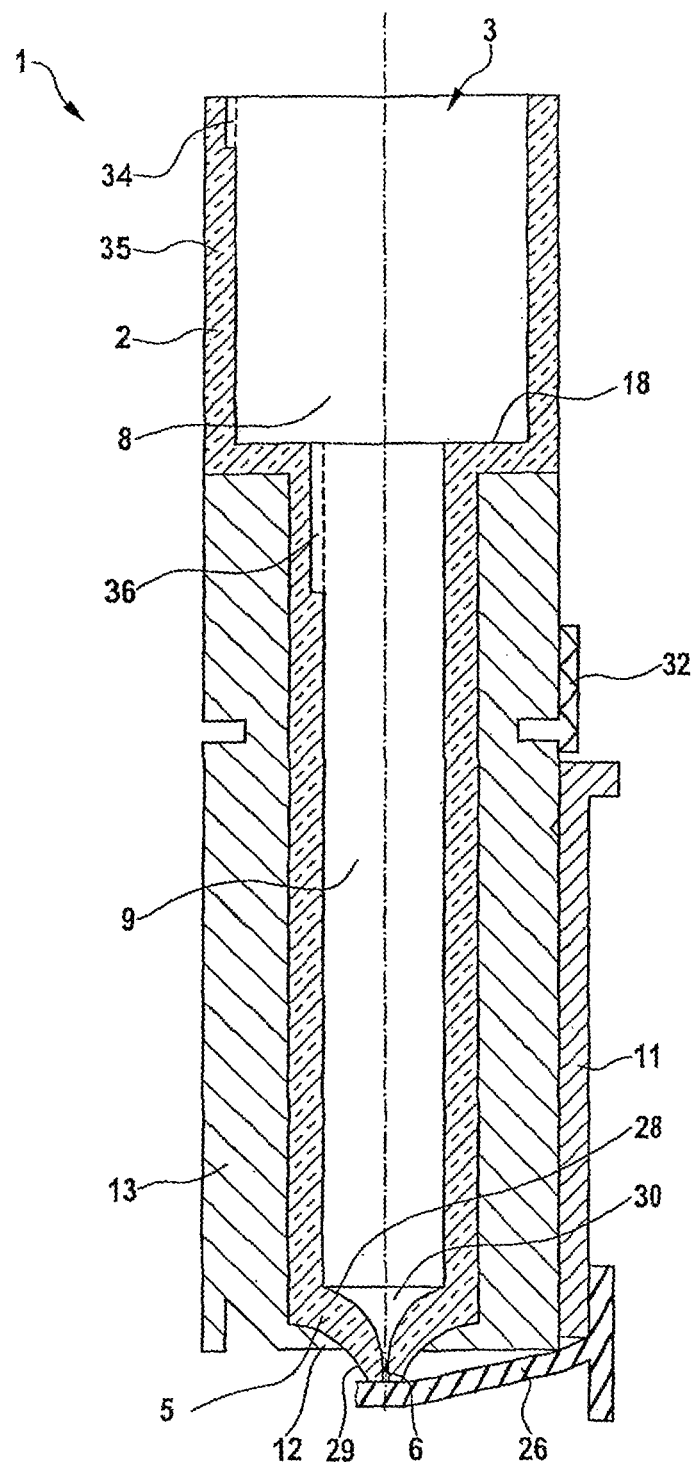
FIG. 2 shows a sectioned side view of a cylinder with two diameters and transfer passages and a pressure-stable outer cylinder of a cylinder-piston unit with a membrane fitted on a closure cap.

FIGS. 1 and 2 illustrate a sectioned side view of a cylinder-piston unit 1. A chamber 3 of a steam- and oxygen-blocking cylinder 2 is formed by a first chamber 8 and a second concentric chamber 9, wherein the cross section of the first chamber 8 is larger than the cross section of the second chamber 9. On the side opposite the first chamber 8, the second chamber 9 is designed with an end wall 5 which has at least one nozzle bore or at least one outlet element 6. Each nozzle bore or each outlet element 6 ends in a raised, truncated cone 29 on the outer side 12 of the pressure-stable outer cylinder 13 encasing the second chamber 9, and has a discharge funnel 30 on its inner side 28 of the end wall 5. On the outer side 12 of the pressure-stable outer cylinder 13 there is a water- and oxygen-blocking membrane 26, for example made of rubber or transparent silicone, which is stretched over the outlet element/elements 6 and is preferably supported by the closure cap 11. As an alternative, the membrane 27 can be fitted on the outer cylinder 13 (see FIGS. 4 and 5). The pressure-stable outer cylinder 13 is designed with optional retaining elements 13, such as a slot 37, threaded flange or bayonet. For example, tension hooks 33 engage in the slot (compare FIGS. 16 and 17).

A transition region, preferably in the form of an annular surface 18, is formed between the first chamber 8 and the second chamber 9. A first configuration of the transition region provides radii (not illustrated) in the transition from the cylindrical wall of the first chamber 8 to the annular surface 18 and from the annular surface 18 to the cylindrical wall of the second chamber 9. A second configuration of said region provides bevels (not illustrated). Further configurations, even combinations of, for example, radii and bevels, a negative or positive camber angle or concave or convex, can be taken into consideration. The configurations firstly assist in the insertion of the injection solution 4 or of the first drug component 14, see FIGS. 4 and 5, and secondly during the production of the cylinder 2 which is produced, for example, by a single-component or two-component plastics injection molding process or from glass. The above-described configurations assist the flow behavior of the steam- and oxygen-blocking material under consideration in order to obtain a cylinder 2 having the predetermined properties, such as perpendicularity, concentricity, wall thickness, etc.

The drug provided for an injection is stored in the cylinder-piston unit 1 for a relatively long amount of time. It is known that drugs are stored in two components until the injection, since, for example, the shelf life is extended. The drug comprising the first drug component 14 and a second drug component 15 is mixed and/or dissolved shortly prior to the injection. The drug component 14 may be a liquid—such as an injection solution 4—or a powder. A lyophilizate is an example of a powdery component. Like the solvent 19, a second drug component 15 is present in liquid form. Other forms of drug components 14, 15 are hereby expressly taken into consideration.

In an alternative embodiment, at the rear end of the chamber 8 and of the chamber 9, at least one freeze-drying passage 34 (in chamber 8) and a transfer passage 36 (in chamber 9) are in each case formed in the cylinder wall 35 (see FIG. 2).

Figure 3:
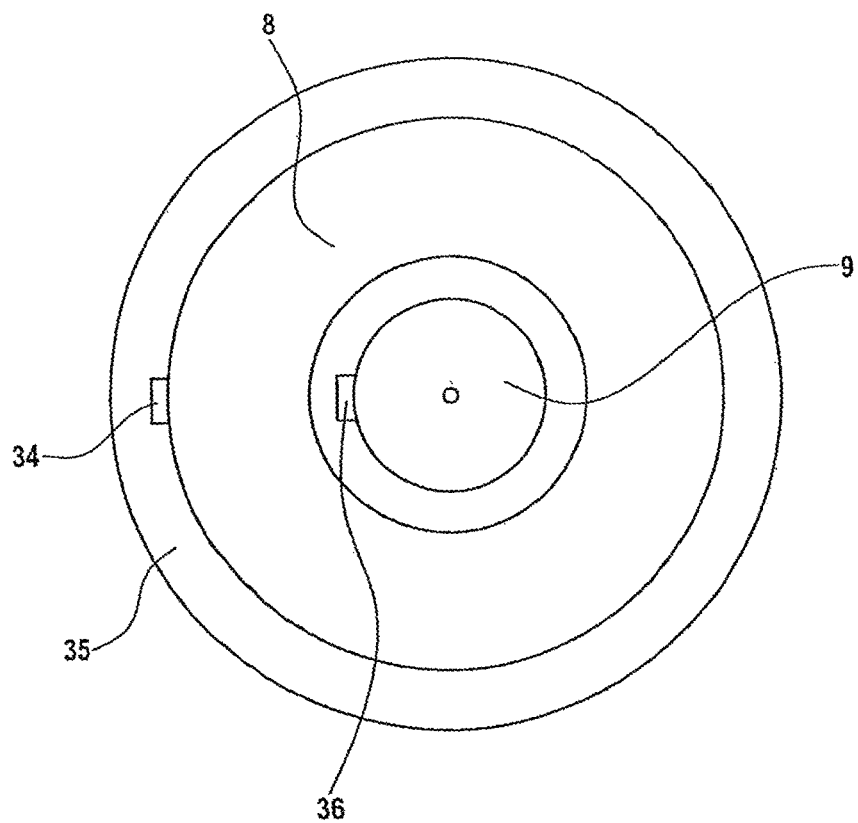
FIG. 3 shows a top view of the position of the passages from FIG. 2.

As viewed from the rear end, the cross section of the freeze-drying passage/freeze-drying passages 34 and of the transfer passage/transfer passages 36 is in the form of a rectangle. However, other shapes are also conceivable, in particular shapes which take into consideration the flow behavior and the strength of the cylinder. See in this regard FIG. 3.

Figure 4:
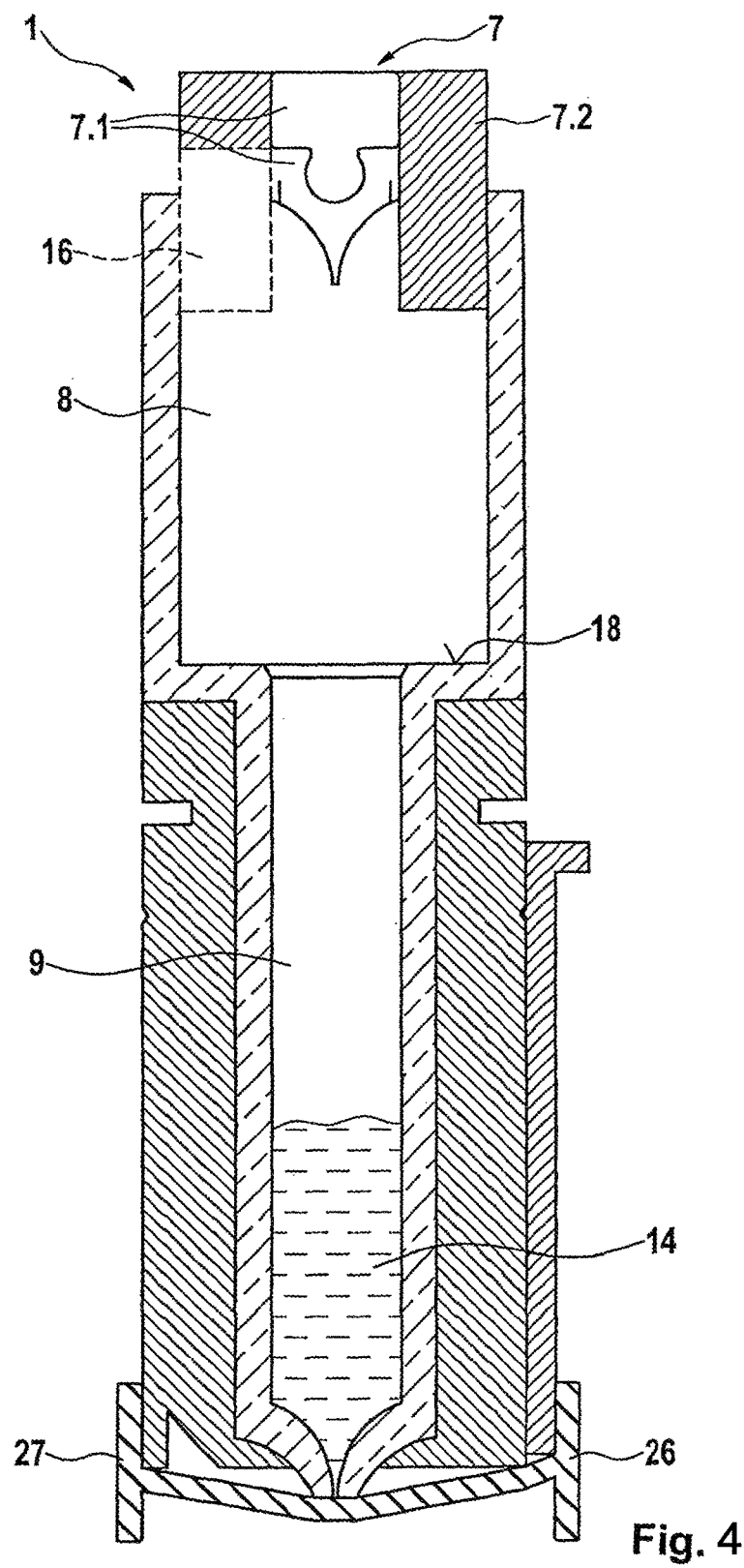
FIG. 4 shows a sectioned side view of the cylinder from FIG. 1 with the injection solution to be lyophilized and the second piston in a position such that the gas space above the injection solution is in contact with the outside.

In a first working section, illustrated in FIG. 4, the sterile first drug component 14 is placed in a sterile manner into the second chamber 9 of the sterile cylinder 2. A sterile second piston 7 is subsequently fitted in a sterile manner into the first chamber 8 in such a manner that a transfer passage 16 between the chamber 3 and the surroundings remains open. The second piston 7 includes a sealing lip 38. With regard to the configuration of the transfer passage 16, see FIGS. 22 to 44.

Figure 5:
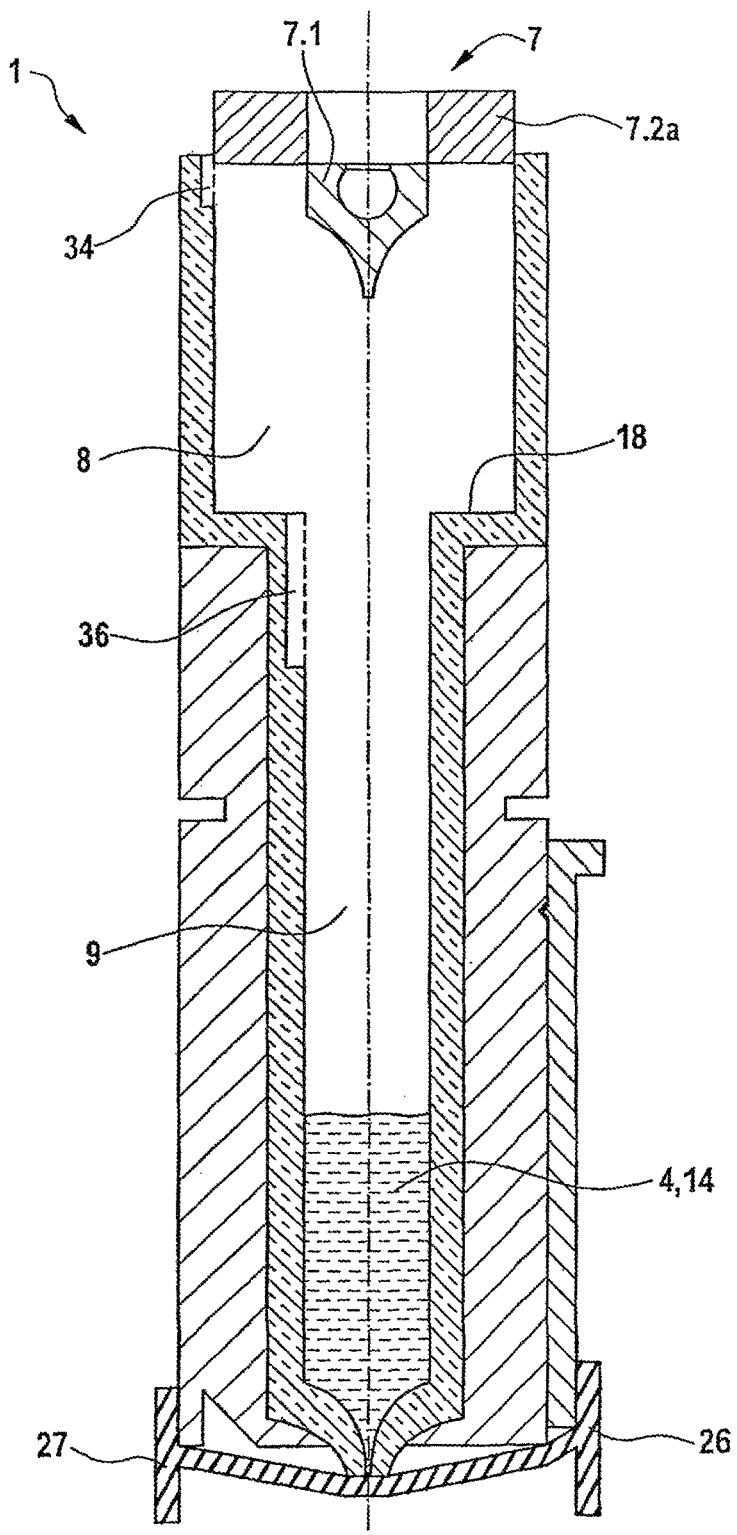
FIG. 5 shows a sectioned side view of the cylinder from FIG. 2 with the injection solution to be lyophilized and the second piston in a position such that the gas space above the injection solution is in contact with the outside.

As an alternative, as illustrated in FIG. 5, a sterile second piston 7 is fitted in a sterile manner into the first chamber 8 in such a manner that the freeze-drying passage 34 in the cylinder wall 35 between the chamber 3 and the surroundings remains open.

All further components and working steps are sterile without this being restated below.

Figure 6:
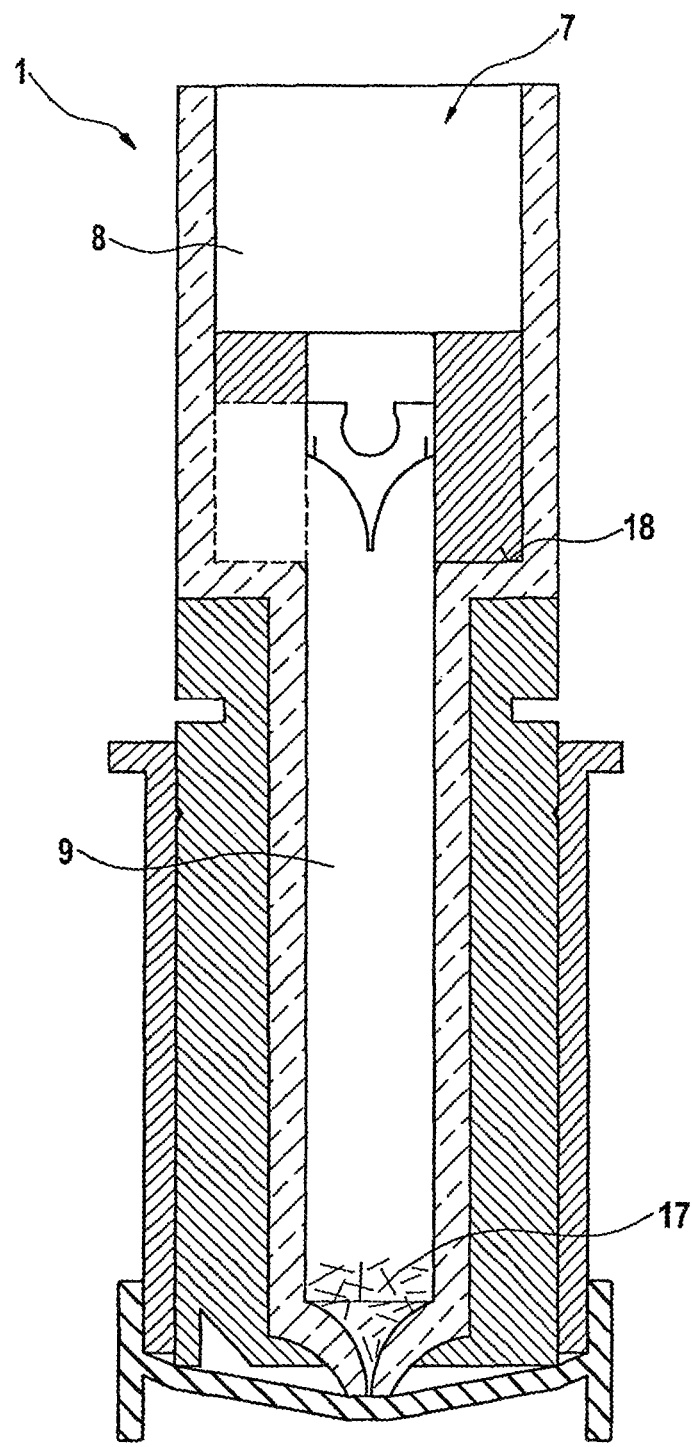
FIG. 6 shows a sectioned side view of the cylinder from FIG. 4 with the second piston sealing the lyophilizate in a sterile and gas-tight manner.
Figure 7:
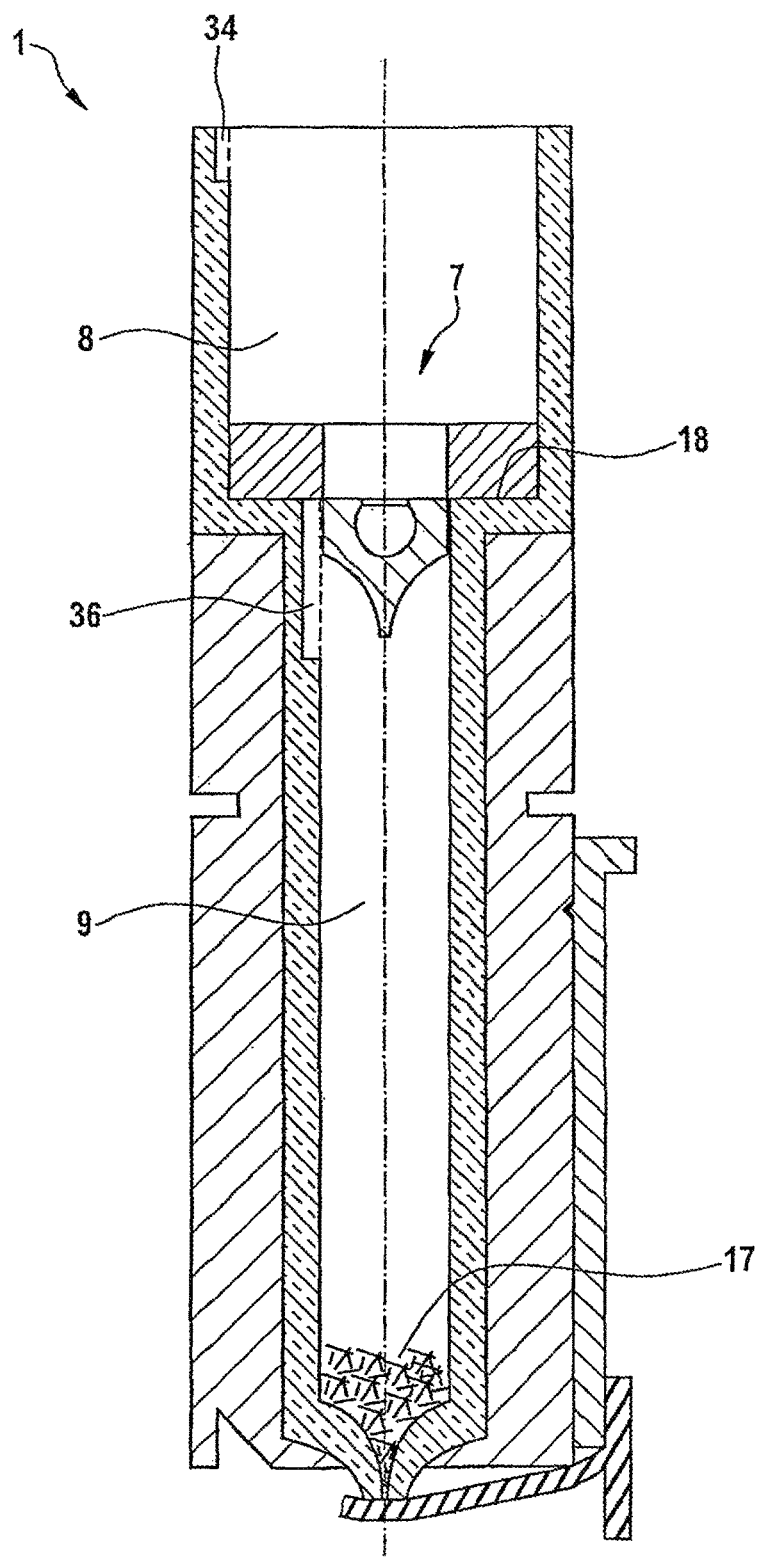
FIG. 7 shows a sectioned side view of the cylinder from FIG. 5 with the second piston sealing the lyophilizate in a sterile and gas-tight manner.

The drug component 14 placed in the second chamber 9 is subsequently freeze-dried and remains in the form of a lyophilizate 17 in the second chamber 9, as illustrated in FIGS. 6 and 7. For storage for a prolonged period of time, the lyophilizate 17 in the second chamber 9 is sealed in a gas-tight and liquid-tight manner. For this purpose, the second piston 7 is pushed into the first chamber 8 in such a manner that the second piston 7 bears against a transition region, the annular surface 18, between the first chamber 8 and second chamber 9.

Figure 8:
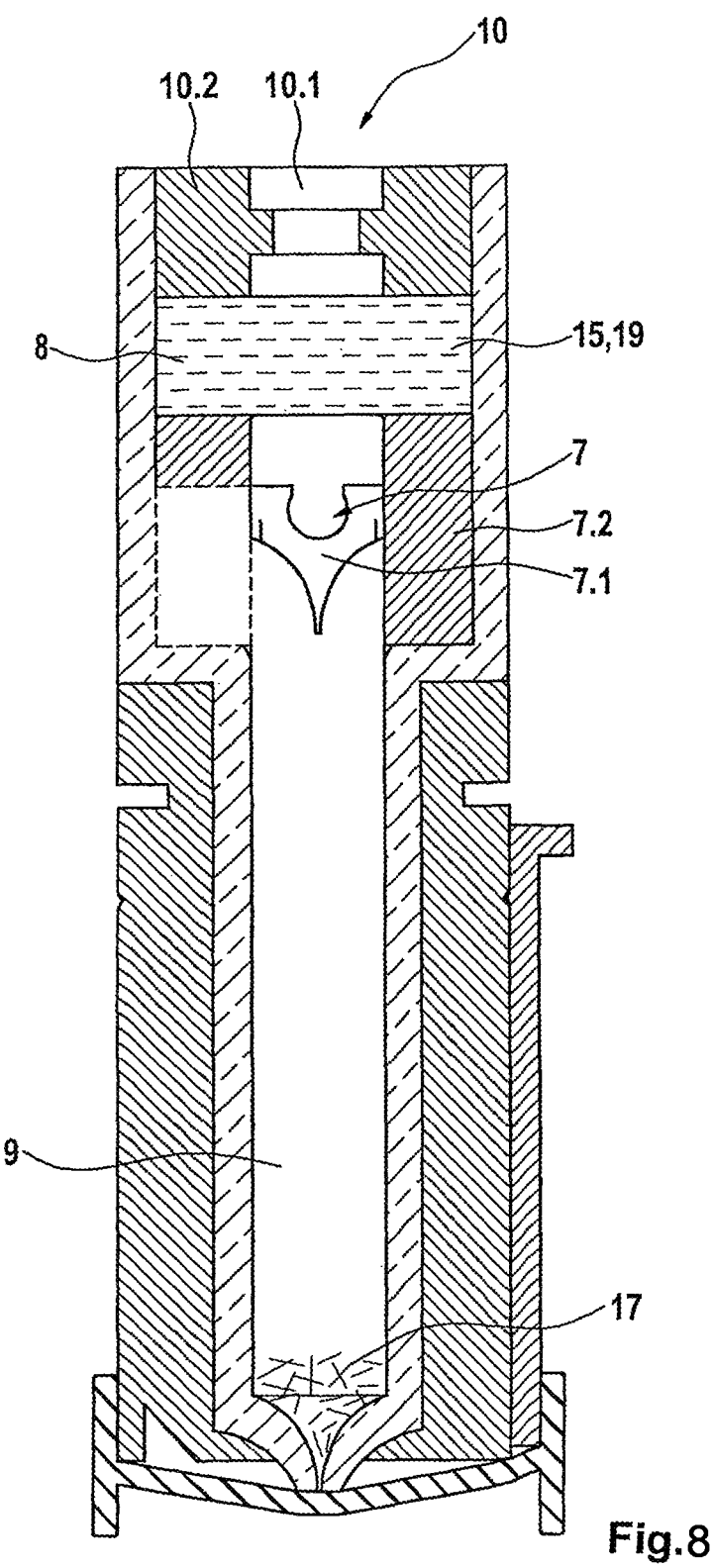
FIG. 8 shows a sectioned side view of the cylinder from FIG. 6 with a solvent and the first piston sealing the latter in a gas-tight and sterile manner.
Figure 9:
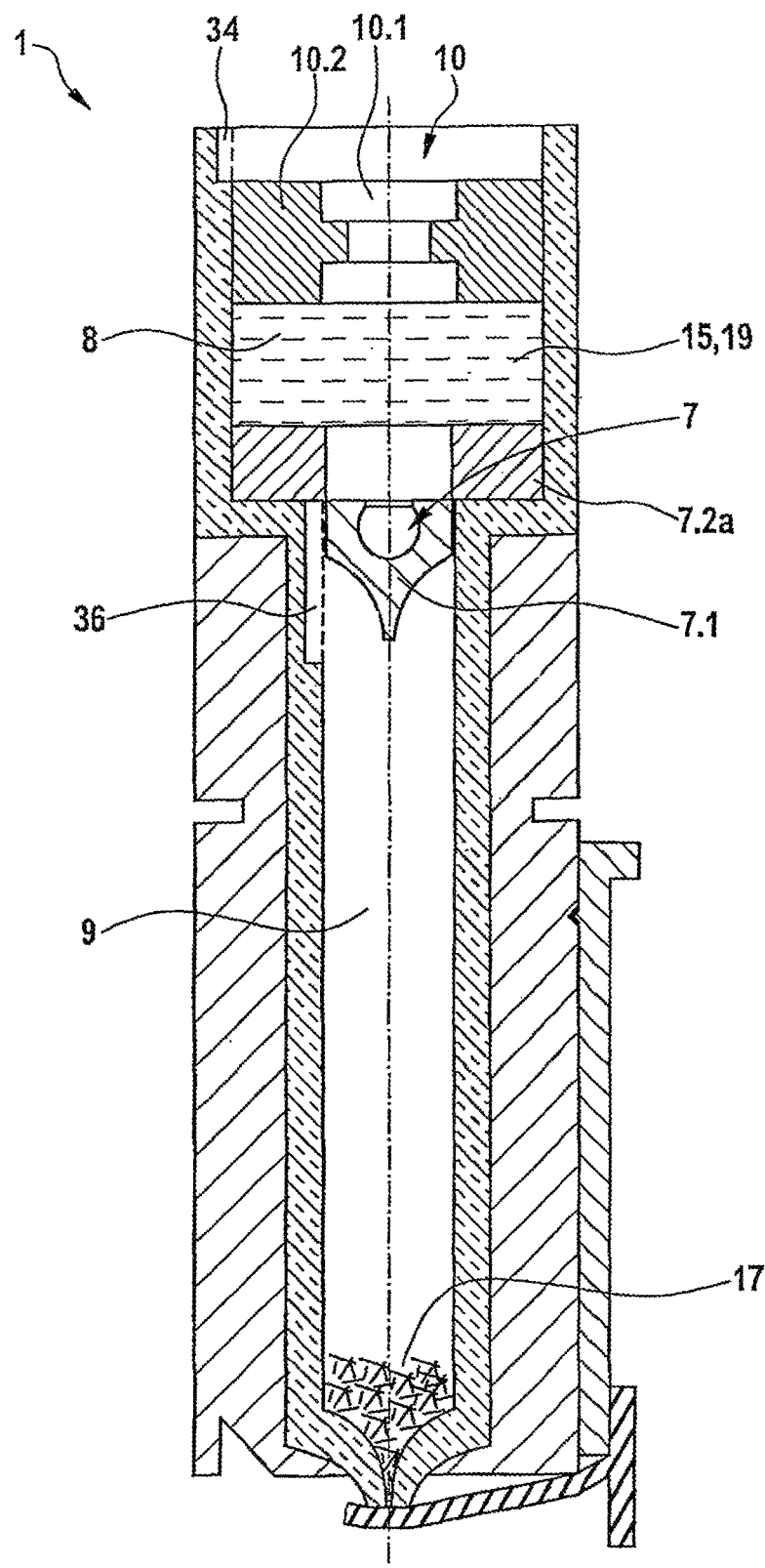
FIG. 9 shows a sectioned side view of the cylinder from FIG. 7 with a solvent and the first piston sealing the latter in a gas-tight and sterile manner.

After the lyophilizate 17 is enclosed in the second chamber 9 by means of the second piston 7, the second drug component 15 of the drug is placed above the second piston 7, and therefore into the first chamber 8, as illustrated in FIGS. 8 and 9. The second drug component 15 is, for example, a solvent 19. In a preferred embodiment, water is used as the solvent 19 and, upon use, is used to dissolve the first component 14 present in the form of a lyophilizate in order to be able to inject a drug present in liquid form—the injection solution 4. After the second component 15 is placed into the first chamber 8, the latter is sealed in a liquid-tight manner by a first piston 10. In this case, the first piston 10 is inserted in an unpressurized manner into the first chamber 8, for example by lateral compression.

The second and the first piston 7, 10 are respectively formed from at least one inner piston body 7.1, 10.1 and one outer piston ring 7.2, 10.2, the inner piston bodies 7.1, 10.1 being arranged in a sliding manner in the outer piston rings 7.2, 10.2. The embodiment which is now present and has two separately sealed chambers 8, 9 serves to store the otherwise unstable injection solution 4 in the form of the lyophilizate 17 which is present separately and the solvent 19 which is likewise present separately.

Before injecting the injection solution 4, it is necessary to mix the lyophilizate 17 with the solvent 19 and to wait for it to dissolve, which may take up to 30 minutes. Only then is the gas cushion 31 which has remained squeezed out by (an) upwardly pointing nozzle(s) 6.

Figure 10:
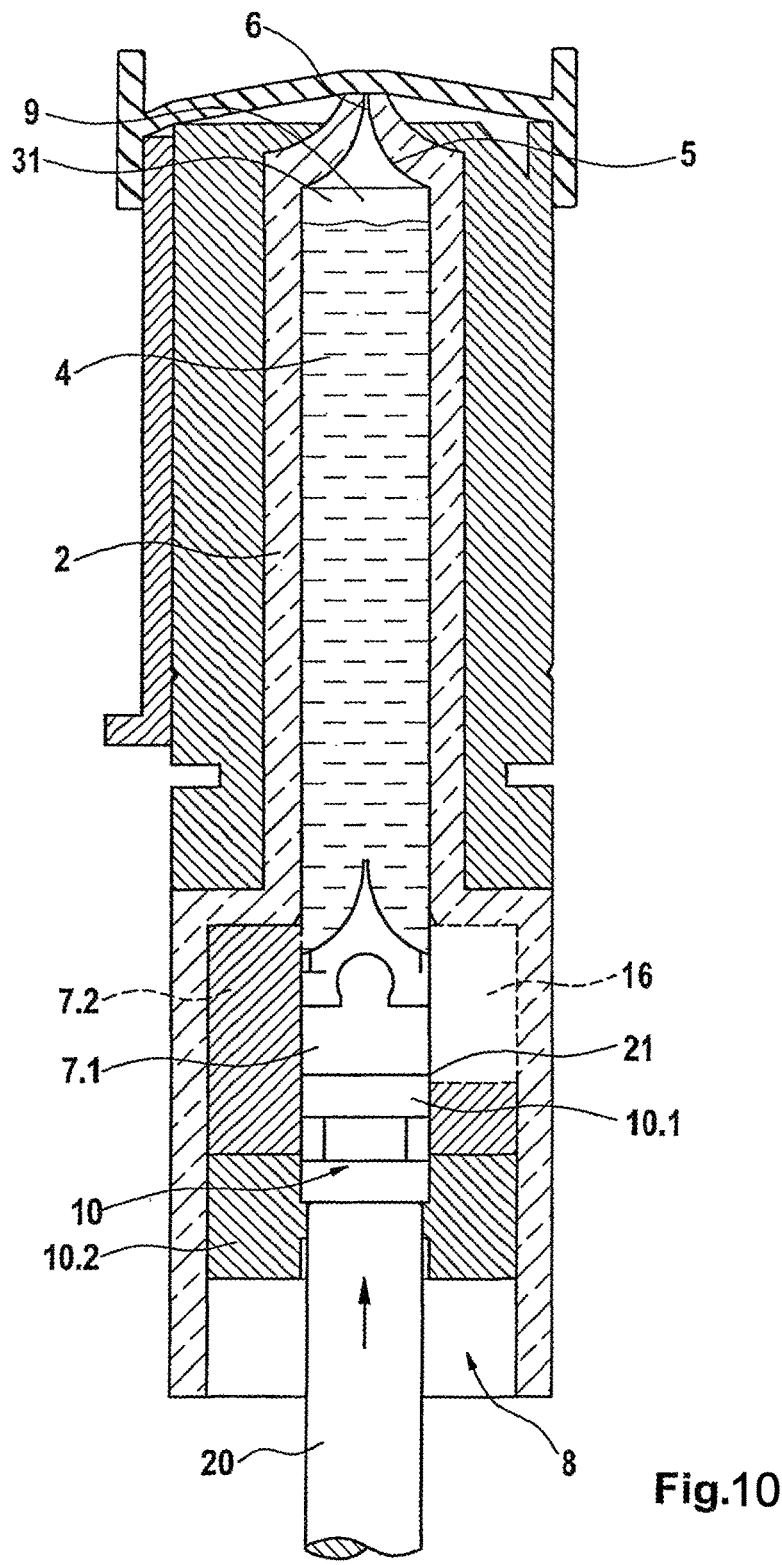
FIG. 10 shows a sectioned side view of the cylinder from FIG. 8 with an open overflow passage, reconstituted injection solution and gas cushion.
Figure 11:
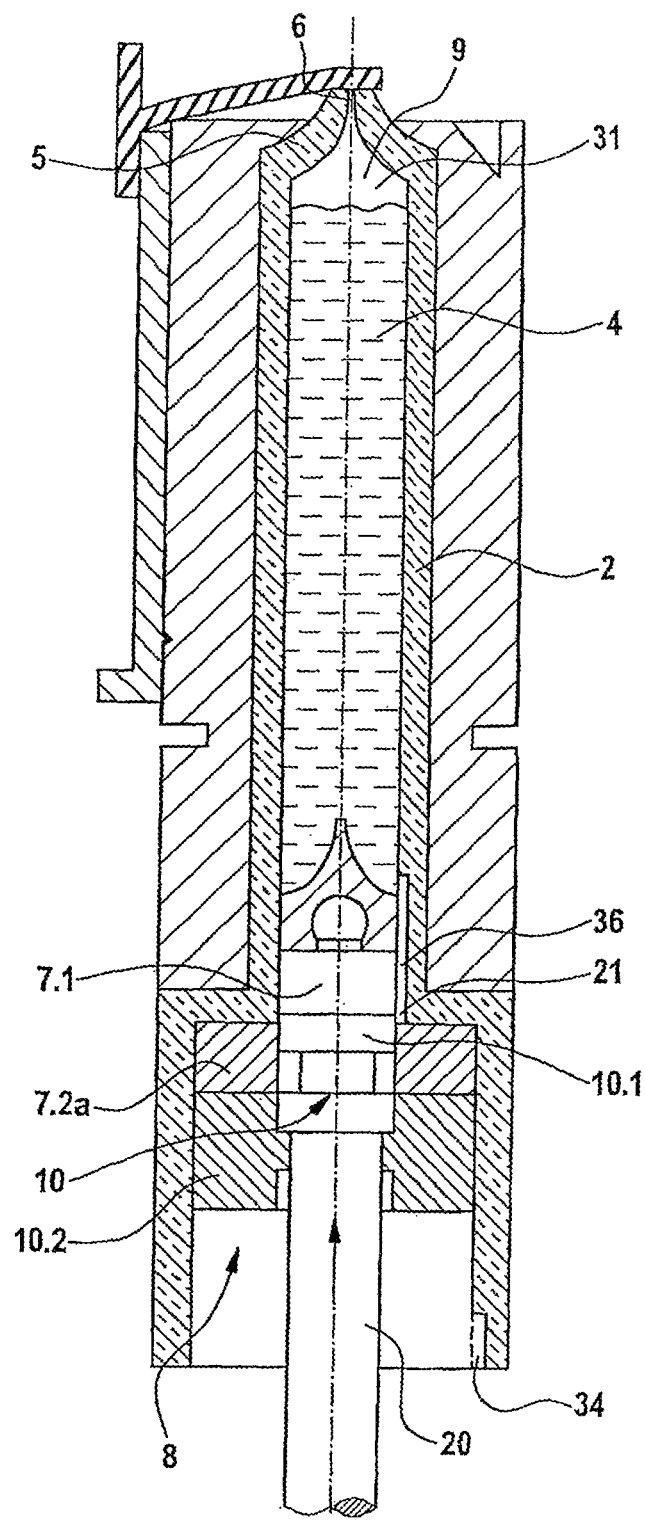
FIG. 11 shows a sectioned side view of the cylinder from FIG. 9 with an open overflow passage, reconstituted injection solution and gas cushion.

FIGS. 10 and 11 illustrate how the solvent 19 passes from the first chamber 8 of the cylinder 2 into the second chamber 9. For this purpose, the cylinder-piston unit 1, which is located in an injector, is preferably rotated through approx. 180° about the horizontal axis. As a result, the gas bubble 31 rises in the direction of the nozzle or outlet element 6. Furthermore, the first piston 10 is moved by means of a piston slide 20, which sits in the injector and is actuated there, in the direction of the end wall 5 of the cylinder 2, as indicated by the arrow. As the first piston 10 is being pushed in, it reduces the size of the first chamber 8, as a result of which pressure is exerted on the second piston 7 via the solvent 19. Since the outer piston ring 7.2 of the second piston 7 rests on the annular surface 18 and cannot be shifted, the pressure applied causes the inner piston body 7.1 of the second piston 7 to be pressed in the direction of the end surface 5. During this manipulation and the subsequent manipulation, the nozzle has to point upward.

At the instant at which the rear edge 21 of the inner piston body 7.1 of the second piston 7 releases the overflow passage 16 formed in the second outer piston ring 7.2, the solvent 19 flows out of the first chamber 8 into the second chamber 9 and mixes with the lyophilizate 17 (first alternative).

At the instant at which the rear edge 21 of the inner piston body 7.1 of the second piston 7 releases the overflow passage 36 formed in the cylinder wall 35, the solvent 19 flows out of the first chamber 8 into the second chamber 9 and mixes with the lyophilizate 17 (second alternative).

The injection solution 4 is available for injection only once the lyophilizate 17 has completely dissolved. In order to improve the dissolving operation, the second chamber 9 is not completely filled with the solvent 19 and the lyophilizate 17. The second chamber 9 also contains a gas cushion 31 which has to be removed by further advancing of the piston slide 20 prior to the injection.

Figure 12:
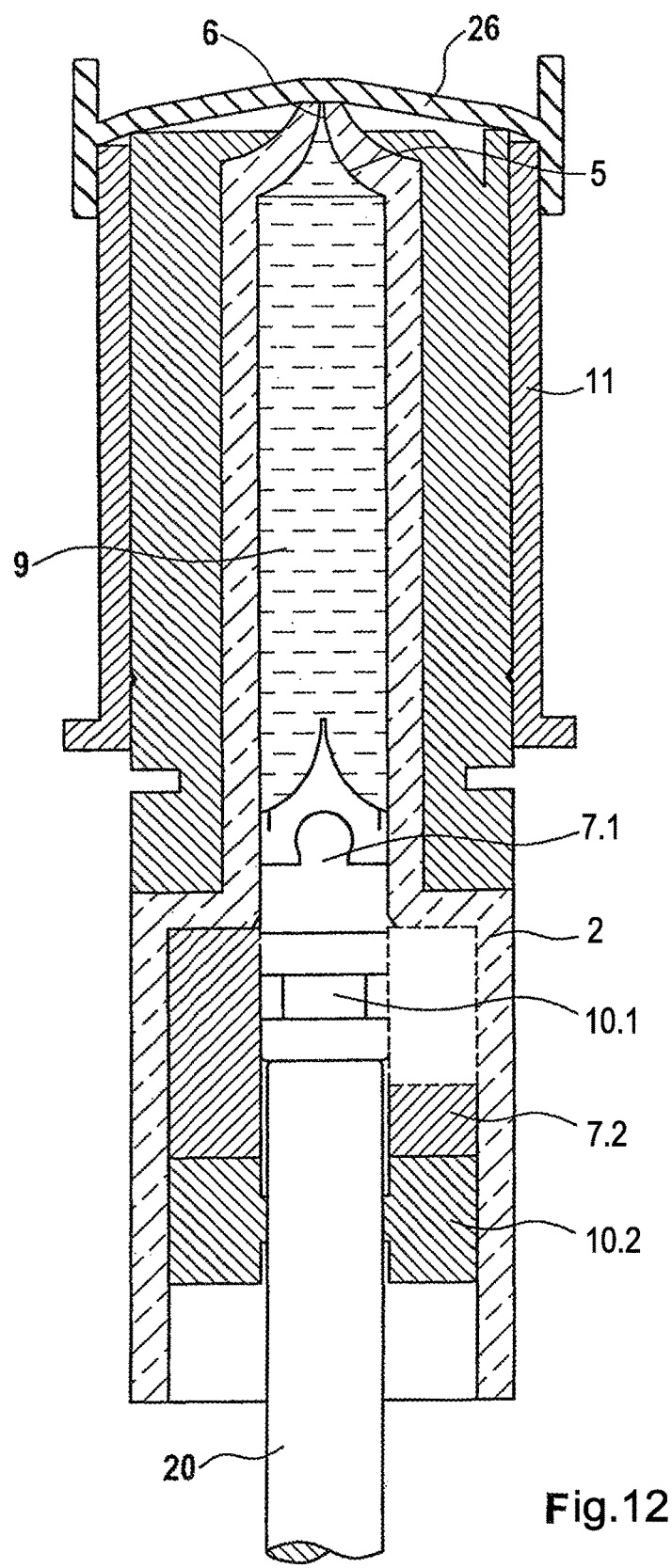
FIG. 12 shows a sectioned side view of the cylinder shown in FIG. 8 with an inner first and inner second piston body advanced to a point free from air bubbles by means of the screwed-in piston slide.
Figure 13:
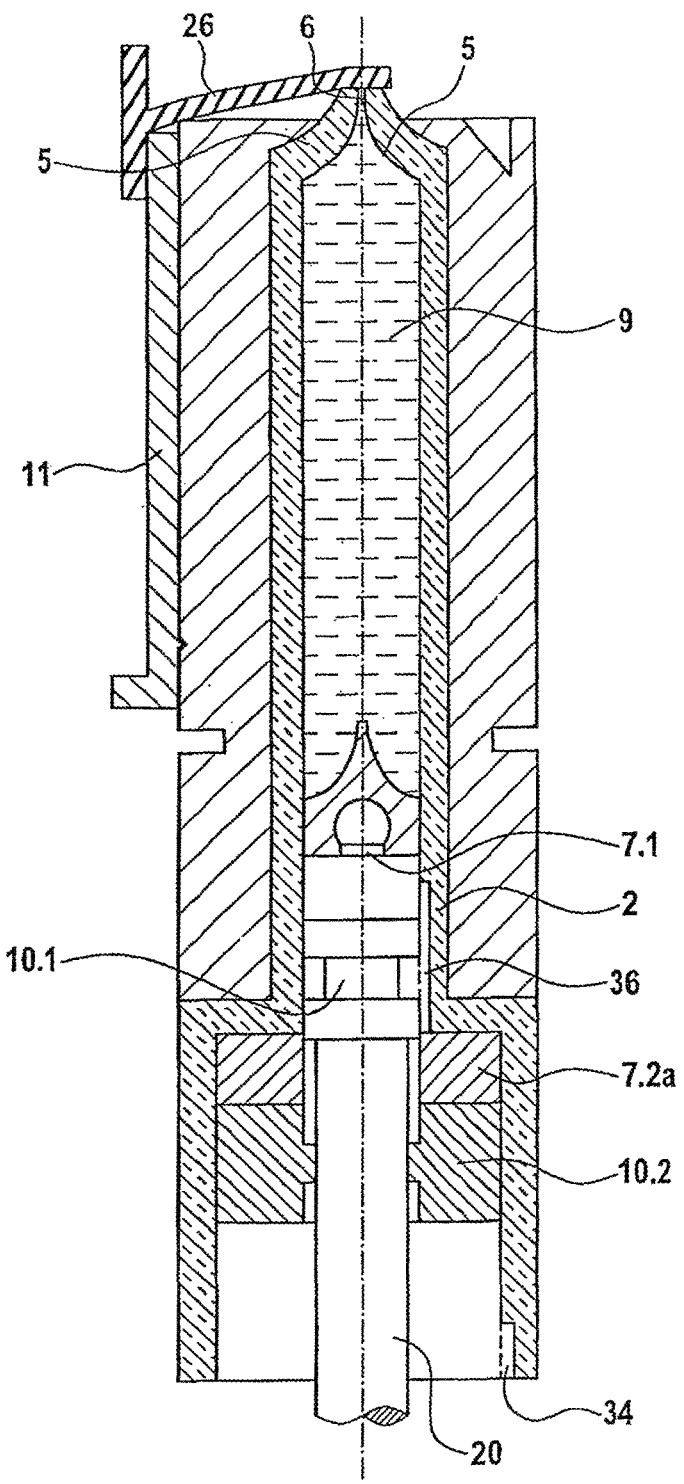
FIG. 13 shows a sectioned side view of the cylinder shown in FIG. 9 with an inner first and inner second piston body advanced to a point free from air bubbles by means of the screwed-in piston slide.

FIGS. 12 and 13 illustrate how the first inner piston body 10.1 is pushed completely into the first chamber 8 of the cylinder 2 and bears against the second inner piston body 7.1 which is already fully inserted in the start of the second chamber 9. The solvent 19 is located completely in the second chamber 9 in the form of an injection solution 4. The piston slide 20 of the injector, which is only partially illustrated in FIG. 15 has hitherto been arranged in the injector in an axially freely and longitudinally displaceable manner. For this purpose, it has a diameter which is smaller than a threaded bore 23 arranged in a flange 22 and smaller than the diameter of the second chamber 9 (see FIGS. 11 and 17). The piston slide 20 is guided axially in the injector, and the region having the smaller diameter is designed in such a manner that when the first inner piston body 10.1 is in the position in which the solvent 19 is conveyed entirely into the chamber 9, that region of the piston slide 20 which has a thread 24 in a complementary manner to the threaded bore 23 is just in contact therewith. Then, by screwing in of the threads, the piston slide 20 is pushed further into the cylinder-piston unit 1, whereupon the air cushion is removed and the energy store transmits force to the piston slide 20. The ejection or squirting-out energy of the disposable injector is brought about, for example, by means of a spring 25.

For this purpose, the first inner piston body 10.1 of the first piston 10 is pushed in the longitudinal direction toward the end wall 5 of the cylinder 2 until the thread 24 of the piston slide 20 can be screwed into the threaded bore 23 of the flange 22. As the piston slide 20 is pushed in and subsequently screwed in, the successively following inner first and second piston bodies 10.1 and 7.1 displace the gas bubble 31 out of the second chamber 9 through the nozzle or the outlet element 6. Upon further screwing in of the piston slide 20, the gas bubble 31 escapes from the second chamber 9, the closure cap 11 being designed with a membrane 26 which releases the nozzle or the outlet element 6 when there is positive pressure in the second chamber 9. The complete squeezing out of the gas bubble from the second chamber 9 by further screwing in of the thread is monitored visually by the user through opposite windows (not illustrated) in the membrane 26 and through the transparent closure cap 11. The solvent 19 can also be caused to flow in even as the then correspondingly longer thread of the piston slide 20 is being screwed in.

Figure 14:
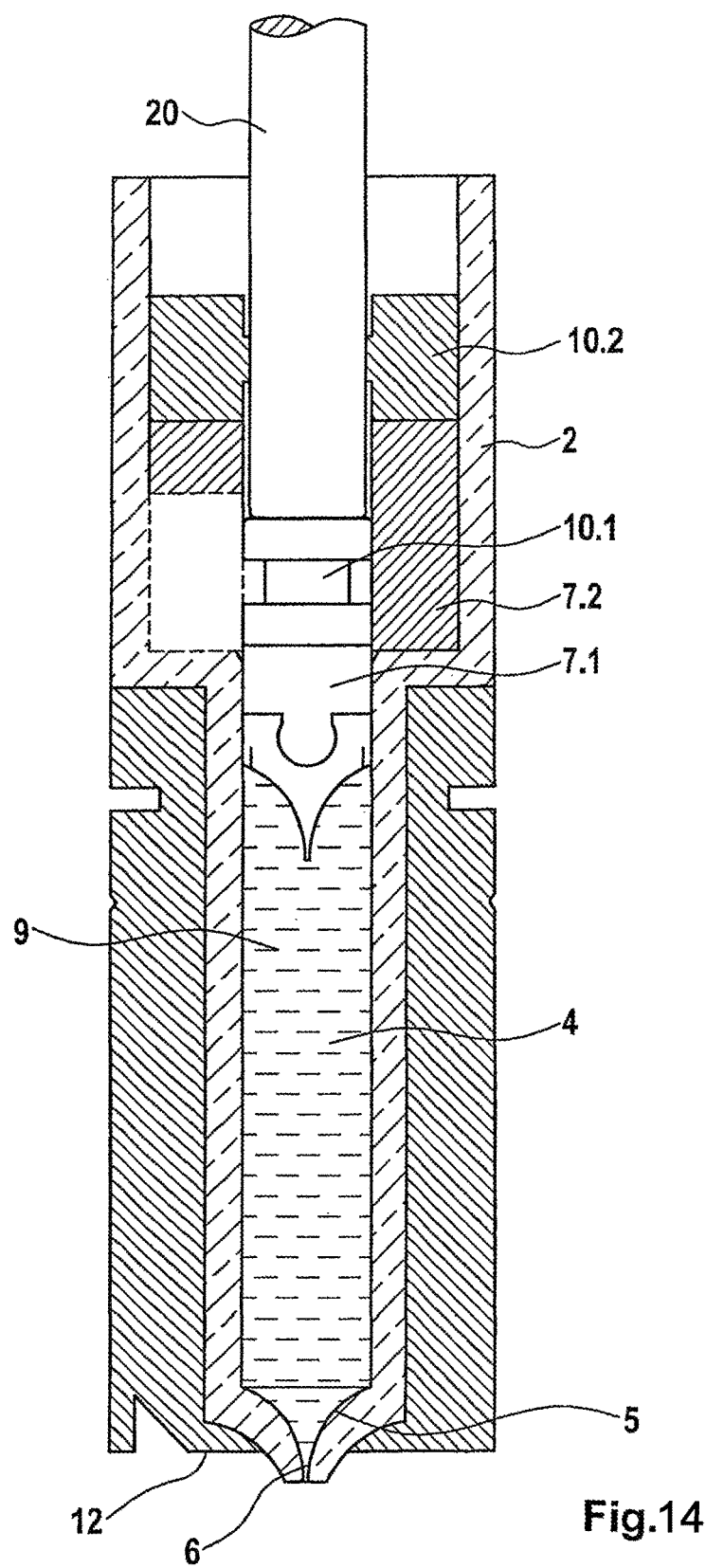
FIG. 14 shows a sectioned side view of the cylinder-piston unit shown in FIG. 12 ready for injection, with the closure cap removed and membrane removed.
Figure 15:
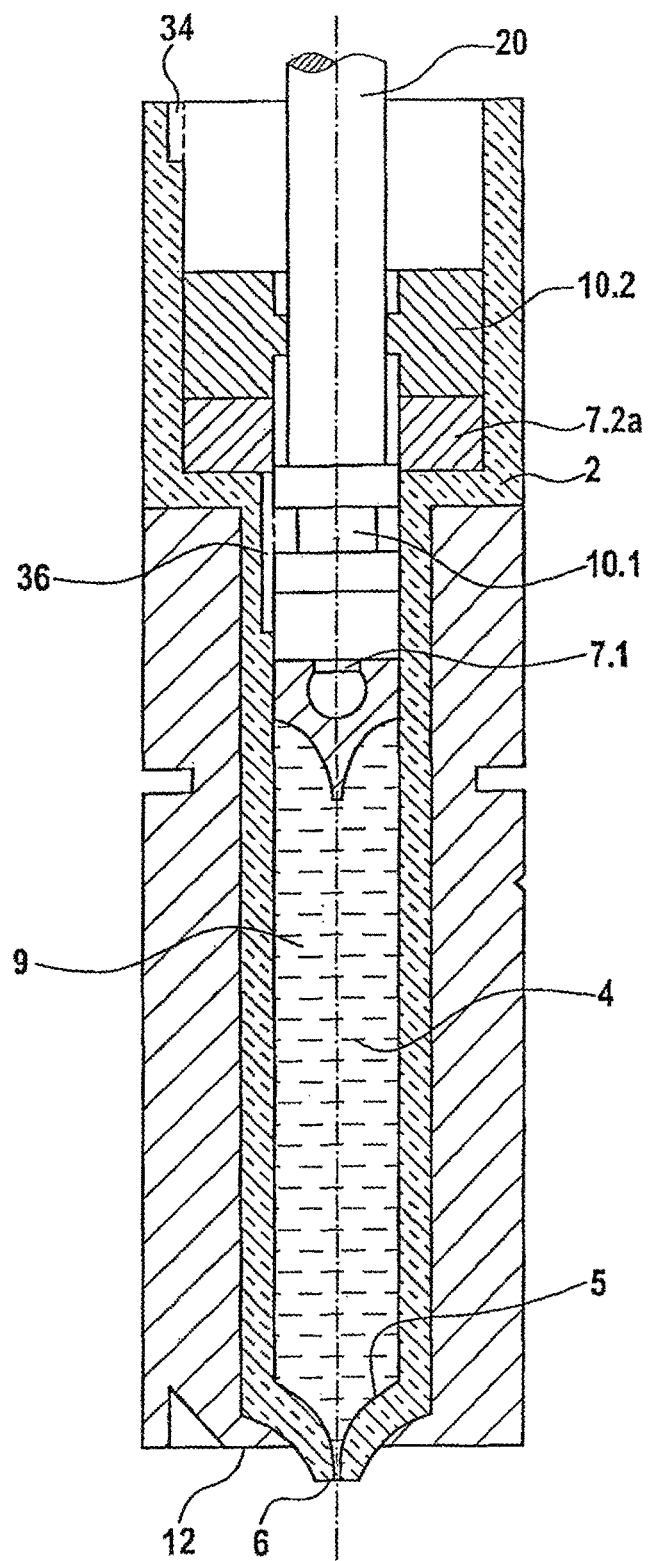
FIG. 15 shows a sectioned side view of the cylinder-piston unit shown in FIG. 13 ready for injection, with the closure cap removed and membrane removed.

To inject the injection solution 4, the closure cap 11 which is latched in place is pulled off the outer cylinder 13. The truncated cone 29 of the outlet element 6 is then pressed against or onto the body part which has been previously disinfected and into which the injection solution 4 is to be injected. By means of a triggering device (not illustrated), the pretensed spring 25 is released, as a result of which the piston slide 20 shoots onto the first inner piston body 10.1 of the first piston 10 and causes the first inner piston body 10.1 and the second inner piston body 7.1 of the second piston 7 in the second chamber 9 to shoot forward in the longitudinal direction onto the end wall 5. The injection solution 4 escapes at a very high speed from the second chamber 9 through the at least one nozzle bore or the outlet element 6, as illustrated in FIGS. 14 and 15.

Figure 16:
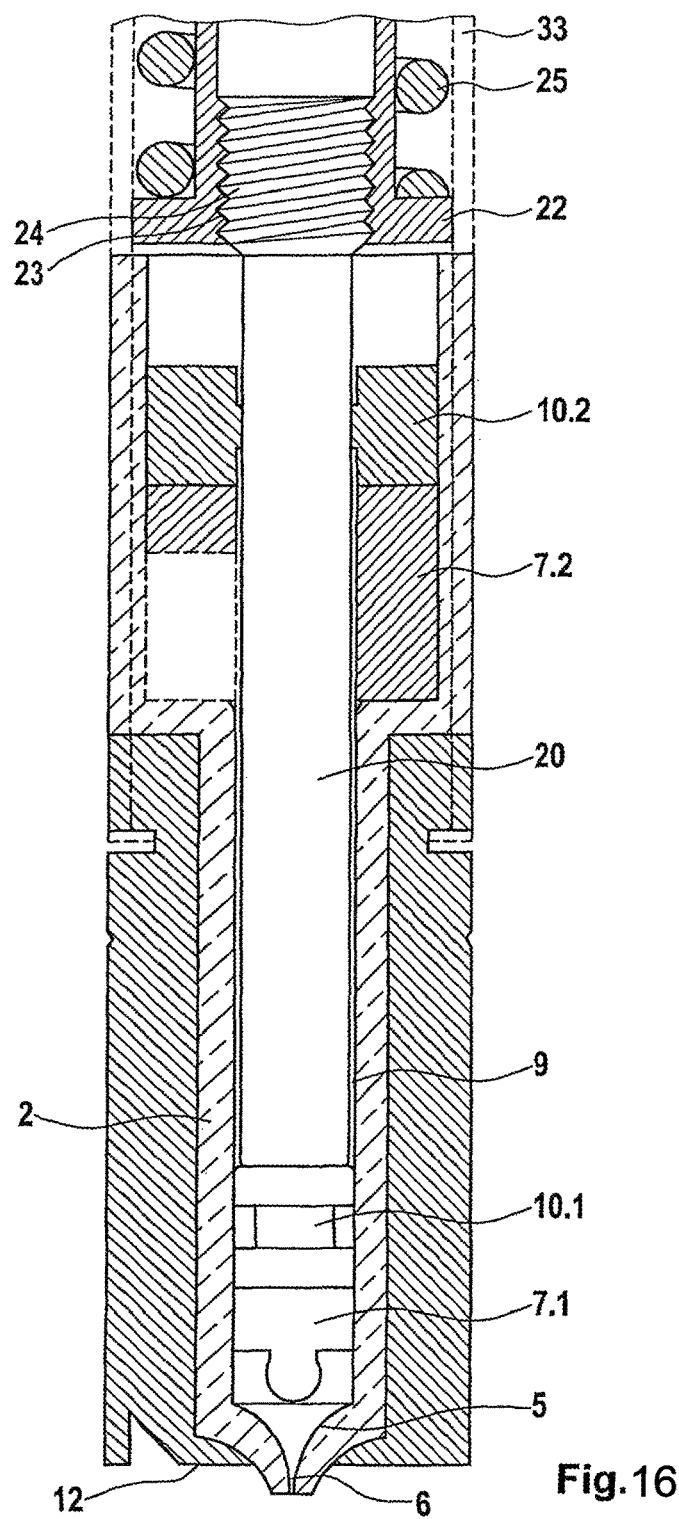
FIG. 16 shows the system show in FIG. 14 following the injection, with the nozzle closed.
Figure 17:
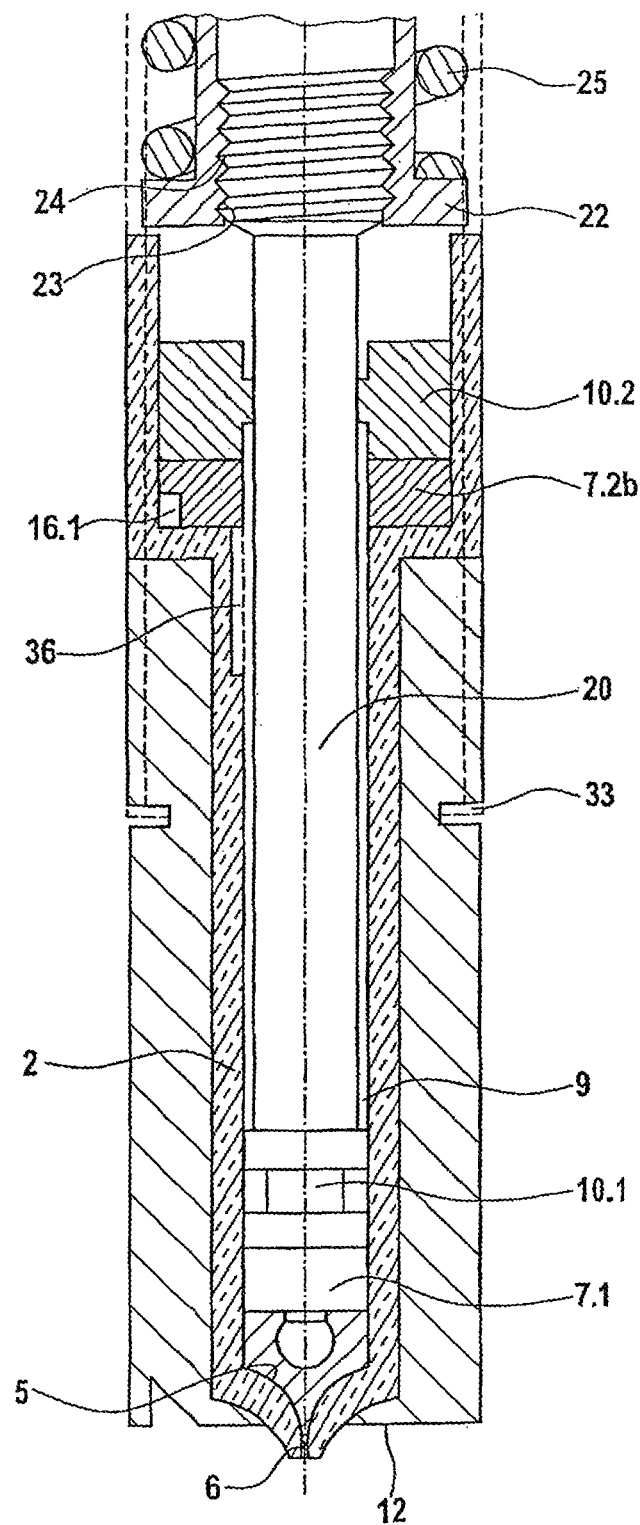
FIG. 17 shows the system show in FIG. 15 following the injection, with the nozzle closed.

When the injection solution 4 has been fully pressed out of the second chamber 9, the second inner piston body 7.1 bears against the end wall 5 and closes the nozzle(s) 6, as illustrated in FIGS. 16 and 17.

FIG. 17 furthermore illustrates an embodiment in which at least one freeze-drying passage 16.1 is formed in a slotted ring 7.2b. The freeze-drying passage 34 which is described further above is functionally replaced by the freeze-drying passage 16.1 illustrated. There is at least one transfer passage 36 in the chamber 9.

It goes without saying that the number of passages 16.1, 34 and 36 can vary. Instead of the transfer passage 36, in a further embodiment at least one transfer passage may also be formed in the second outer piston ring 7.2. There is therefore the option, depending on requirements or possibility, to form the passages either only in the cylinder wall 35 or in the cylinder wall 35 and the second outer piston ring 7.2.

Figure 18:
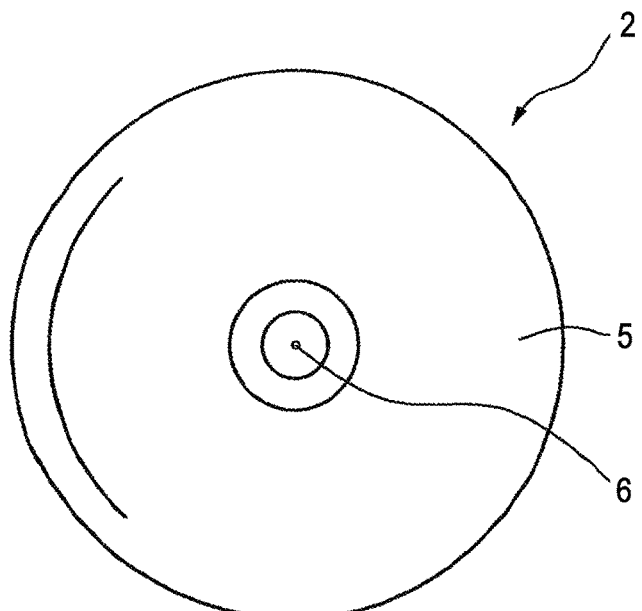
FIG. 18 shows a bottom view of the cylinder-piston unit with one nozzle.

FIG. 18 shows a bottom view, i.e. from the front end toward the rear end of the cylinder-piston unit 1, a version of the cylinder-piston unit 1 with a truncated cone 29 and a nozzle 6.

Figure 19:
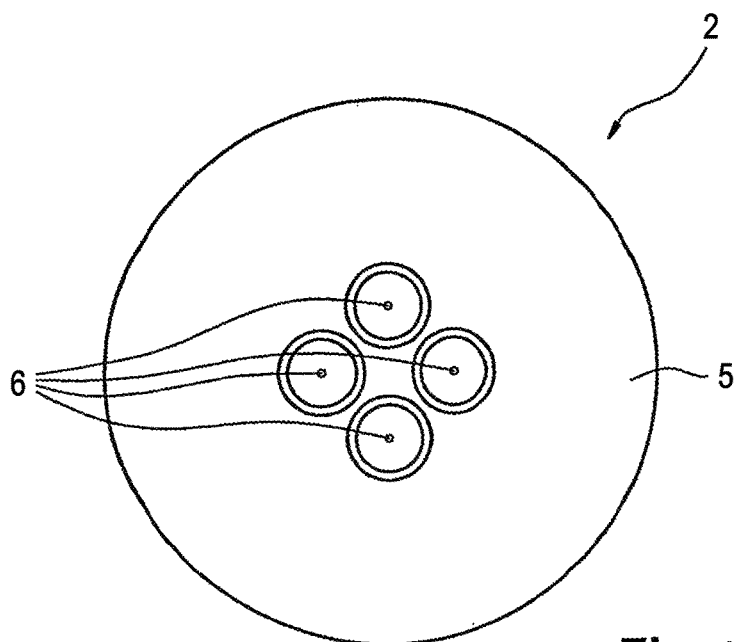
FIG. 19 shows a bottom view of the cylinder-piston unit with four nozzles.

FIG. 19 shows a bottom view of a version of the cylinder-piston unit 1 with four truncated cones 29 and four nozzles 6.

Figure 20:
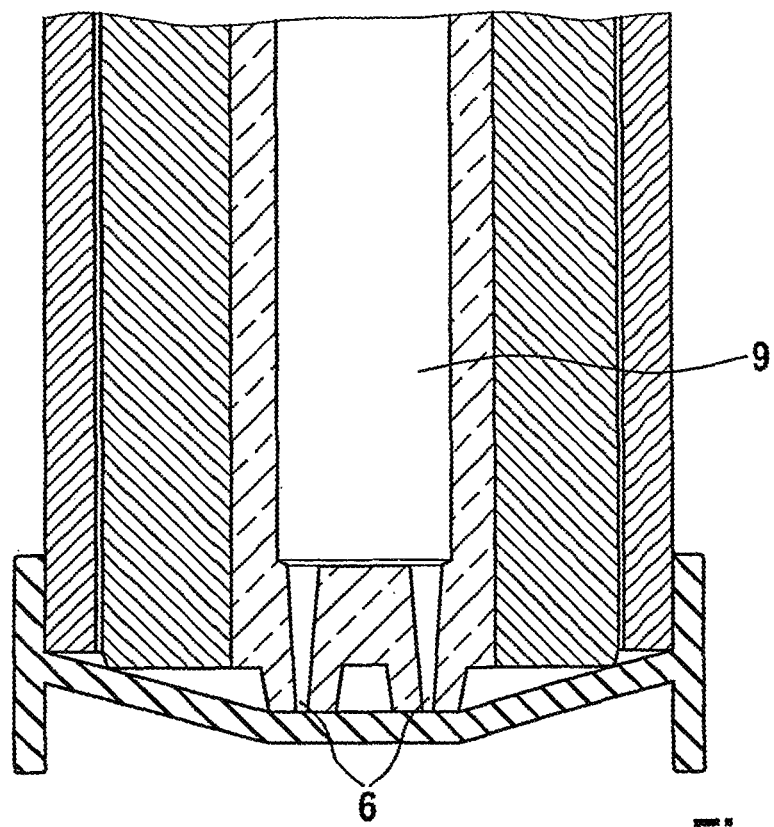
FIG. 20 shows a cross section of a the cylinder-piston unit with four nozzles through two diagonally opposite nozzles.

The version from FIG. 19 is illustrated in cross section in FIG. 20 where two diagonally opposite outlet elements 6 are located in the vertical section plane.

FIGS. 21 to 44 illustrate the second outer piston ring 7.2 with the transfer passage 16 formed differently in each case. The second inner piston body 7.1 is not illustrated.

Figure 21:
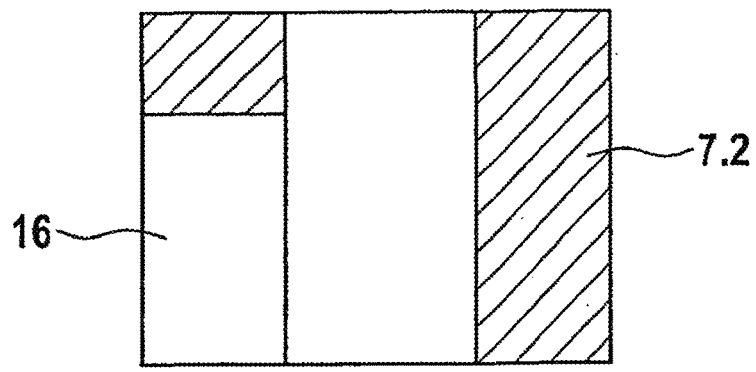
FIG. 21 shows a sectioned side view of the second outer piston ring with a trifunctional passage.
Figure 22:
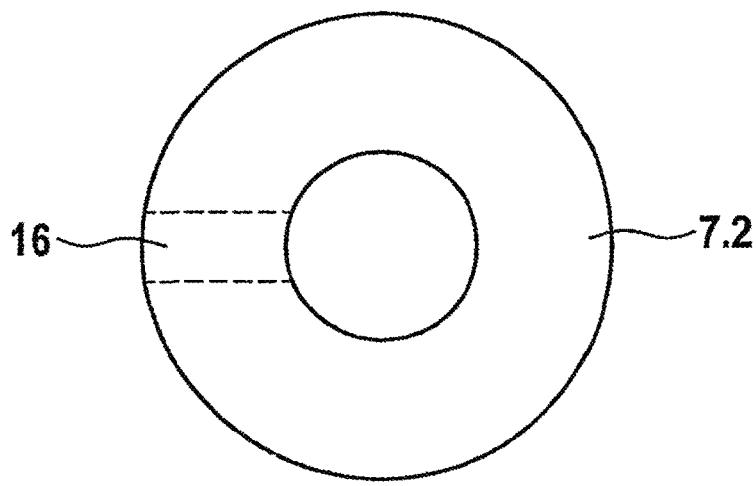
FIG. 22 shows a plan view of the second outer piston ring with a trifunctional passage shown in FIG. 21.
Figure 23:
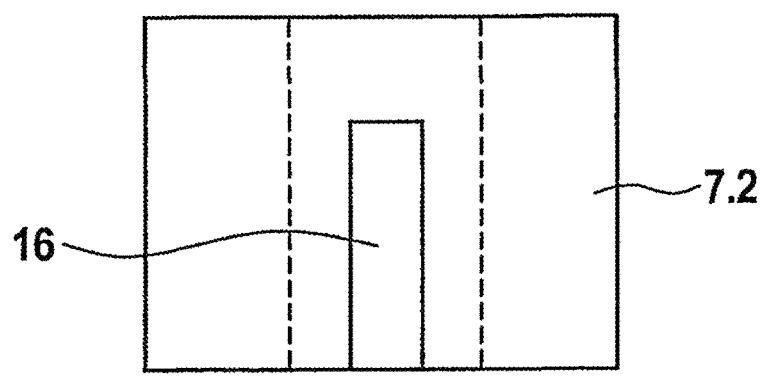
FIG. 23 shows an elevation of the second outer piston ring with a trifunctional passage shown in FIG. 21.

The first function of the second outer piston ring 7.2 illustrated in FIG. 21 can be seen in FIG. 4. The chamber 3, which comprises a first chamber 8 and second chamber 9, of the cylinder-piston unit 1 is connected to the surroundings or to the outside through the open transfer passage 16 such that freeze-drying can take place. The second function—steam-proof sealing of the lyophilizate in the second chamber 9—can be seen in FIGS. 6 and 8. Finally, the third function of the second outer piston ring 7.2 with the transfer passage 16, which is also referred to as a bypass, can be seen in FIG. 10. The solvent 19, preferably water, passes through said transfer passage out of the first chamber 8 into the second chamber 9 in which the lyophilizate 17 is located. The second outer piston ring 7.2 which is illustrated in half section (at the top), in top view (center) and in a front view (at the bottom)—but rotated forward through 90 degrees—shows one possible design of the transfer passage 16 which here has a width which is smaller than the inside diameter and a height which corresponds to approximately ⅔ of the entire height.

Figure 24:
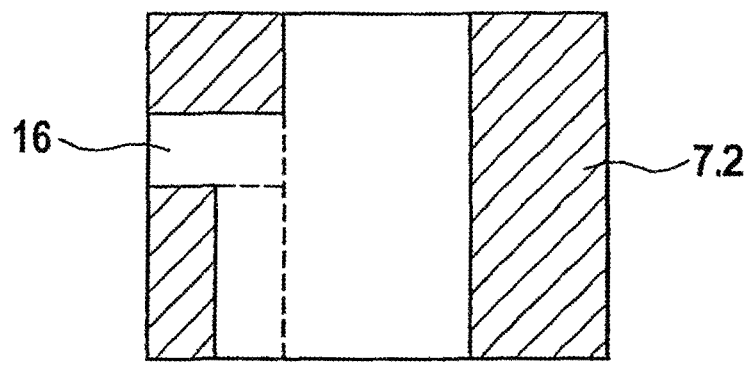
FIG. 24 shows a sectioned side view of the second outer piston ring with a trifunctional passage as in FIG. 21, but with a smaller dead volume and having greater mechanical stability.
Figure 25:
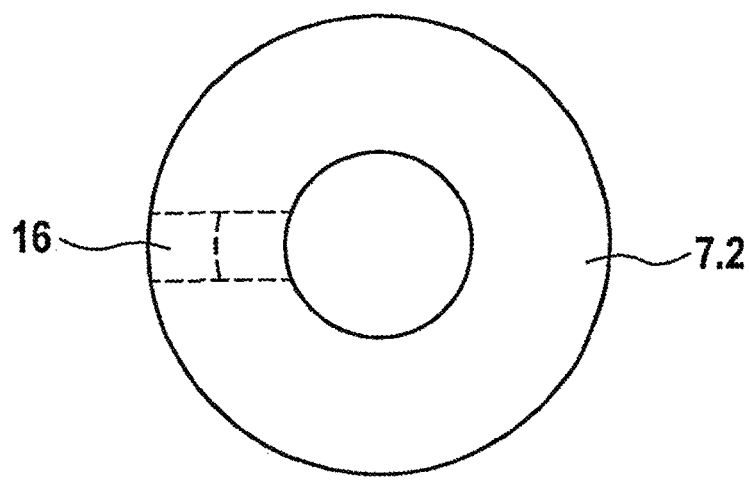
FIG. 25 shows a plan view of the second outer piston ring with a trifunctional passage as in FIG. 24.
Figure 26:
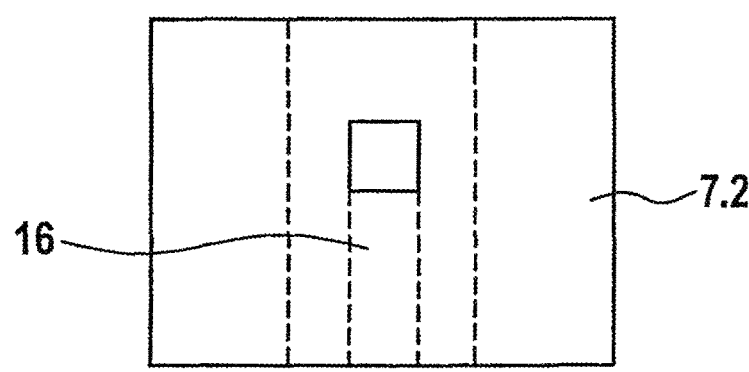
FIG. 26 shows an elevation of the second outer piston ring with a trifunctional passage as in FIG. 24.

A further design is illustrated in FIG. 24. The effect achieved by this configuration is a smaller dead volume and greater mechanical stability. For this purpose, the second outer piston ring 7.2 obtains a radially outwardly pointing, square or alternative (for example round) window, arranged approximately halfway up the second outer piston ring 7.2, and an axially parallel passage which corresponds to the window and has the width of the window and a depth extending as far as the mean radius.

Figure 27:
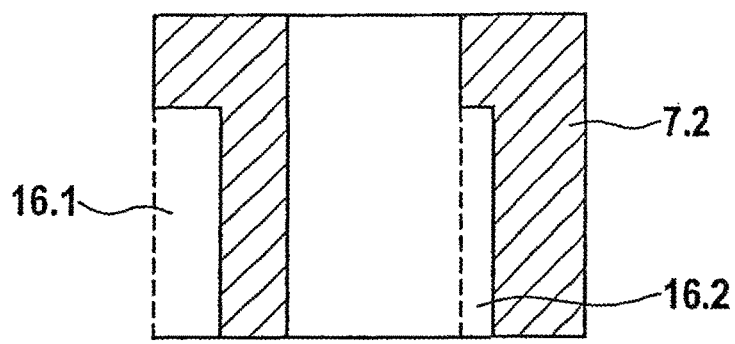
FIG. 27 shows a sectioned side view of the second outer piston ring with a functionally separated freeze-drying passage and overflow passage.
Figure 28:
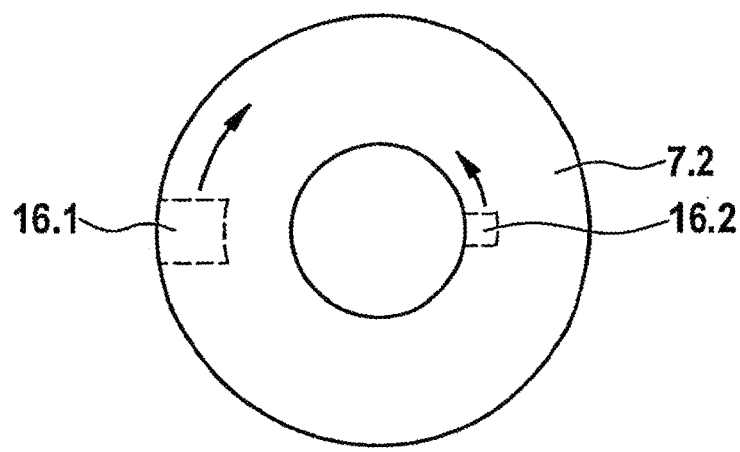
FIG. 28 shows plan view of the second outer piston ring with a functionally separated freeze-drying passage and overflow passage as shown in FIG. 27.
Figure 29:
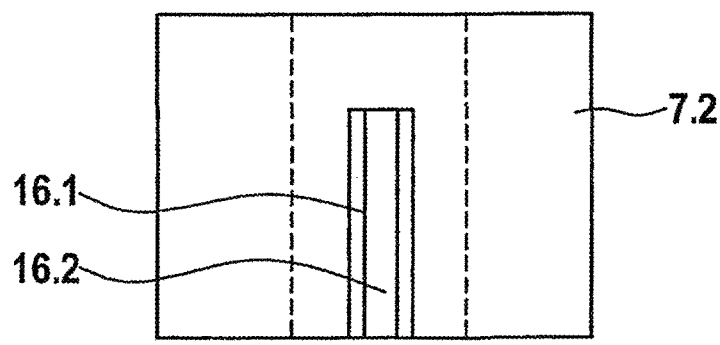
FIG. 29 shows an elevation of the second outer piston ring with a functionally separated freeze-drying passage and overflow passage as shown in FIG. 27.

A second outer piston ring 7.2 designed with two functionally separate transfer passages 16 is illustrated in FIG. 27. In this case, an outer transfer passage 16.1 (freeze-drying passage) is in operation during the freeze-drying and an inner transfer passage 16.2 (overflow passage) is in operation during the transfer of the solvent 19. The two transfer passages 16.1, 16.2 can be at any angle to each other, as seen in the axial direction, the upper annular surface opposite the outer side 12 of the cylinder-piston unit 1 being closed. A plurality of transfer passages 16.1, 16.2 can also be formed. This enables, for example, the freeze-drying speed and the flow speed of the solvent 19 during the transfer from the first chamber 8 into the second chamber 9 to be influenced. The height of the transfer passages 16.1, 16.2 corresponds preferably to ½ to ⅔ of the height of the second outer piston ring 7.2, the heights of the respective transfer passages 16.1, 16.2 not having to be equal, however.

Figure 30:
FIG. 30 shows a sectioned side view of the trifunctional second outer piston ring in an alternative embodiment as a quad ring.
Figure 31:
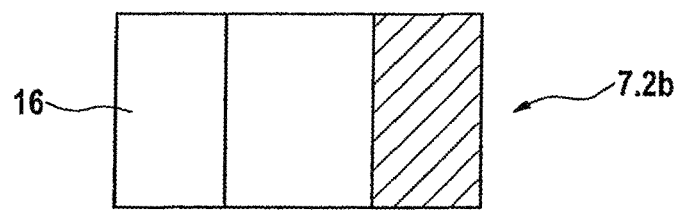
FIG. 31 shows a sectioned side view of the trifunctional second outer piston ring in an alternative embodiment as a slotted ring.
Figure 32:
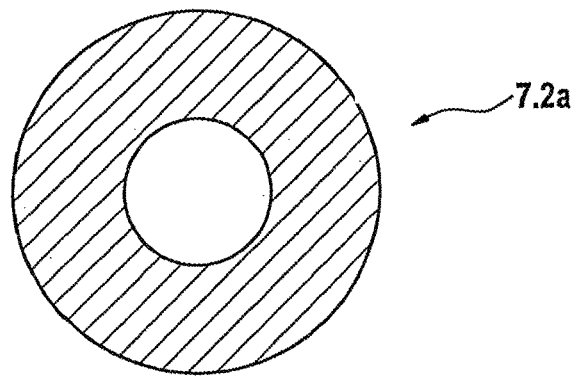
FIG. 32 shows a plan view of the trifunctional second outer piston ring in an alternative embodiment as a quad ring shown in FIG. 30.
Figure 33:
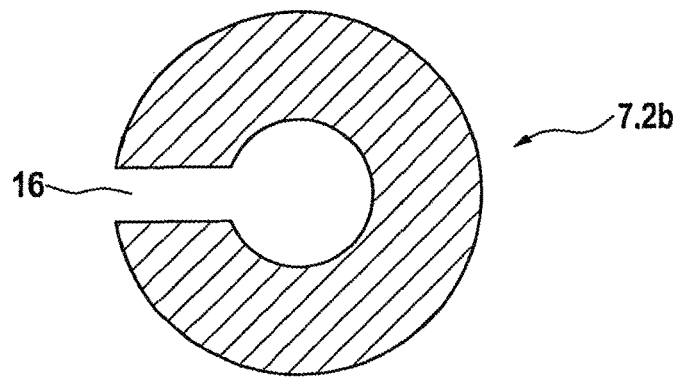
FIG. 33 shows a plan view of the trifunctional second outer piston ring in an alternative embodiment as a slotted ring shown in FIG. 31.

FIG. 30 shows the second outer piston ring 7.2 from FIG. 21 in a two-part embodiment. The upper part 7.2a comprises a closed quad ring (hollow cylinder); the lower part 7.2b comprises a quad ring (hollow cylinder) with a continuous slot 16. The trifunctional piston rings 7.2 shown in FIGS. 24 and 27 may also be of two-part design.

Figure 34:
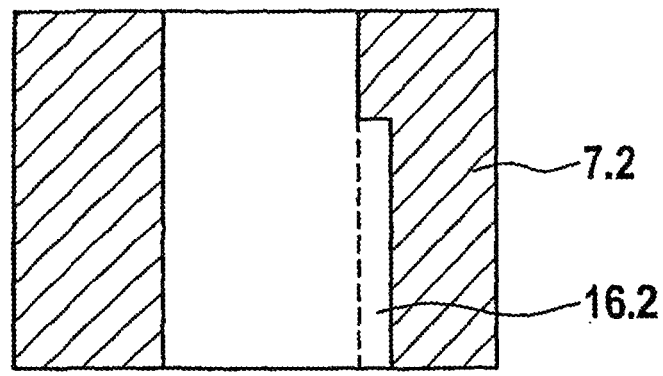
FIG. 34 shows a sectional view of a second outer piston ring with a bifunctional passage.
Figure 35:
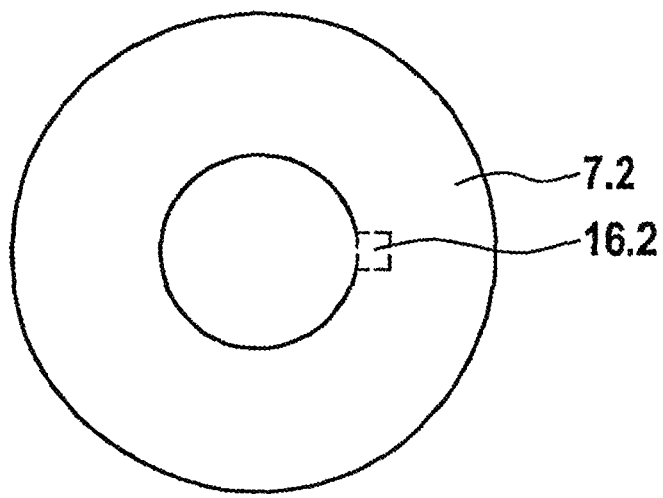
FIG. 35 shows a plan view of a second outer piston ring with a bifunctional passage shown in FIG. 34.
Figure 36:
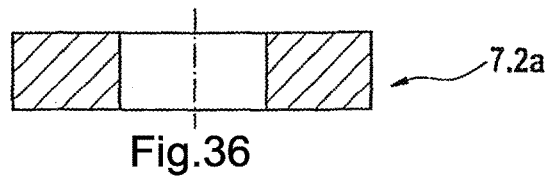
FIG. 36 shows a sectioned side view of the bifunctional second outer piston ring from FIG. 34 in an alternative embodiment, as a quad ring.
Figure 37:
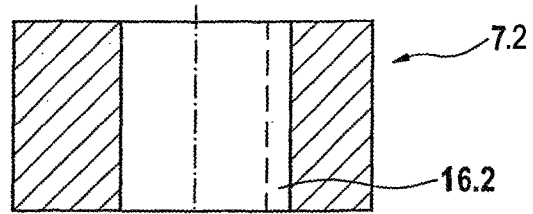
FIG. 37 shows a sectioned side view of the bifunctional second outer piston ring from FIG. 34 in an alternative embodiment, as a transfer passage ring.
Figure 38:
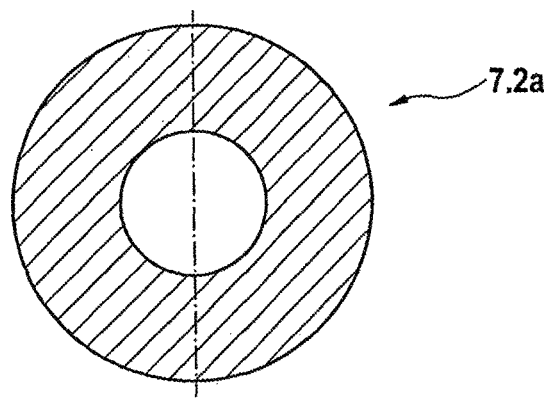
FIG. 38 shows a plan view of the bifunctional second outer piston ring shown in FIG. 36.
Figure 39:
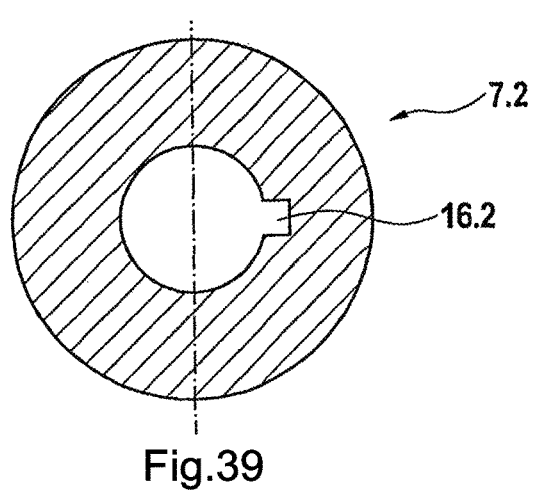
FIG. 39 shows a plan view of the bifunctional second outer piston ring shown in FIG. 37.

FIG. 34 illustrates a second outer piston ring 7.2 with a bifunctional transfer passage 16.2 which can be produced together with the second inner piston body 7.1 by a normal piston jig after the freeze-drying. The second inner piston body 7.1 together with the connected second outer piston ring 7.2 then seals the lyophilizate 17 present in the second chamber 9 in a manner analogous to the illustration in FIG. 8. The second function as a transfer passage 16.2 for the solvent 19 is analogous to FIG. 10.

The form of the second outer piston ring 7.2 of FIG. 34 from two parts is illustrated in FIGS. 36 to 39.

Of course, in the case of all of the second outer piston rings 7.2, the overflow passage 16.2 can be closed not only at the upper end, but also at the lower end—i.e. on both sides.

Figure 40:
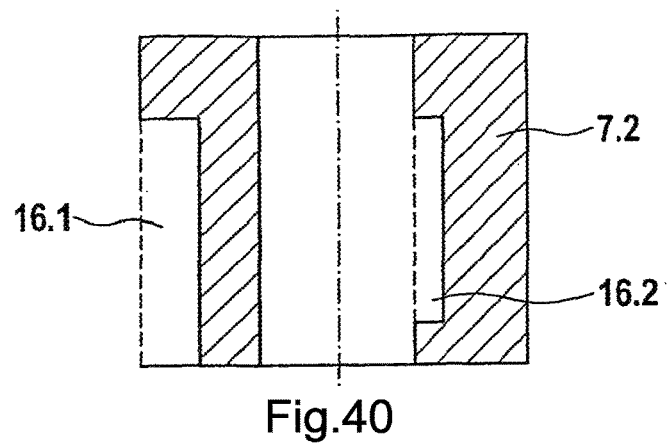
FIG. 40 shows a sectioned side view of the second outer piston ring from FIG. 27 with an overflow passage closing on both sides.
Figure 41:
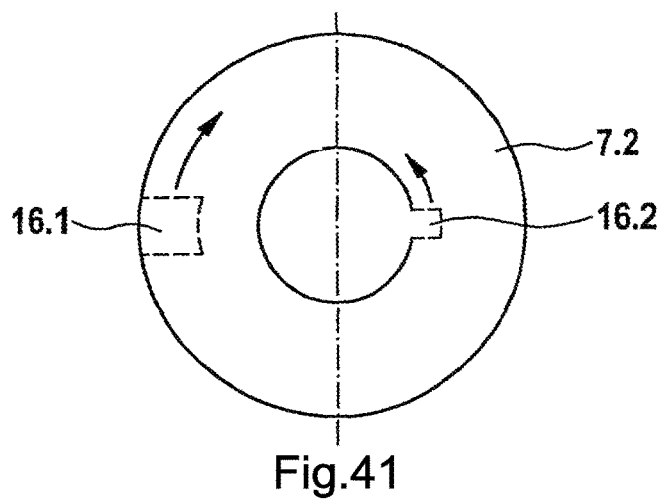
FIG. 41 shows a plan view of the second outer piston ring from FIG. 40.
Figure 42:
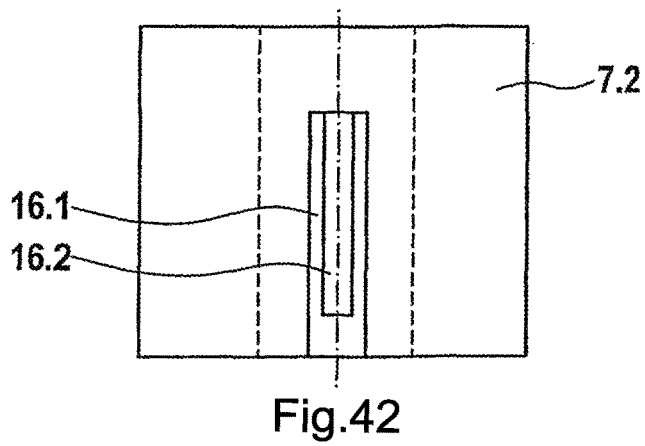
FIG. 42 shows an elevation of the second outer piston ring from FIG. 40.

FIG. 40 thus shows the second outer piston ring 7.2 of FIG. 14, in which the overflow passage 16.2 is supplemented by a closed part. By contrast, the freeze-drying passage 16.1 also has to run on so as to be open at the bottom.

Figure 43:
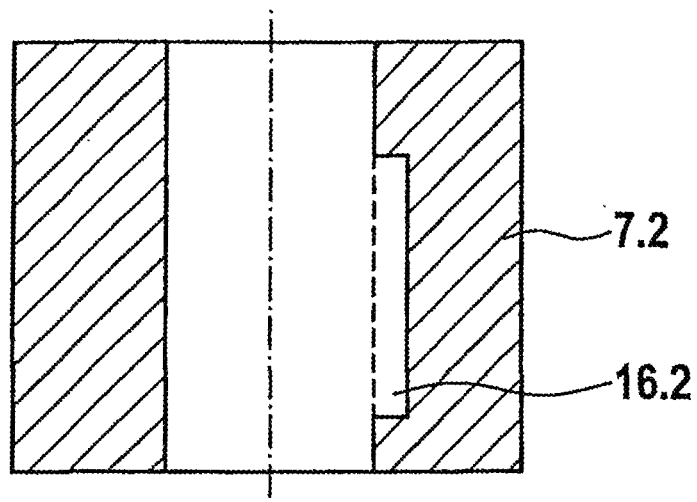
FIG. 43 shows a sectioned side view of the second outer piston ring from FIG. 34 with an overflow passage closing on both sides; and, FIG. 44 shows a plan view of the second outer piston ring from FIG. 34 with an overflow passage closing on both sides.
Figure 44:
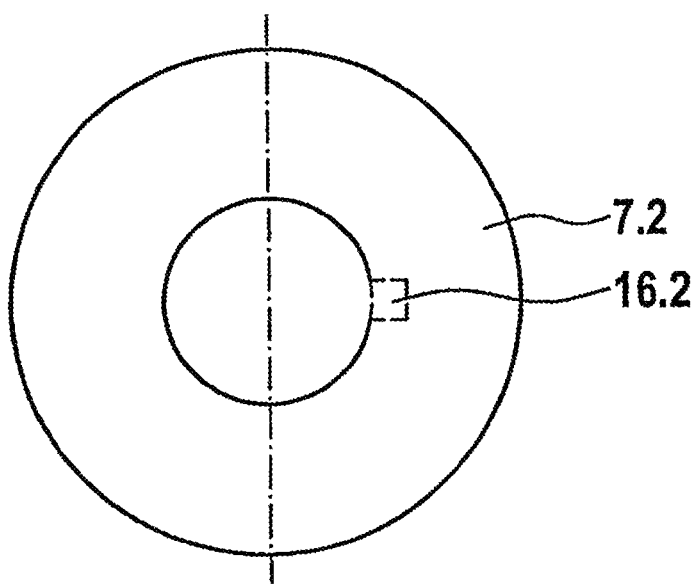

FIG. 43 shows, as an example, the bifunctional overflow passage 16.2 of FIG. 34 with a closed extension.

The corresponding method of the present invention for filling the cylinder-piston unit (1) for a needle-free disposable injector is applicable where the cylinder-piston unit (1) comprises a piston-cylinder unit (1) for a needle-free injector, for example for providing a sterile injection solution, with a chamber (3) which is arranged in a cylinder (2) and is intended for receiving an injection solution (4), an end wall (5) with at least one nozzle bore or an outlet element (6), and a second piston (7) arranged movably in the chamber (3), chamber (3) of two-part design with a first chamber (8) and a concentric second chamber (9), the cross section of the first chamber (8) being larger than the cross section of the second chamber (9), the first chamber (8) formed such that it is closed by a first piston (10) and the second chamber (9) formed such that it is closed by the second piston (7), the first chamber (8) being separated from the second chamber (9), and the second piston (7) formed with at least one transfer passage (16), or the first chamber (8) formed with at least one closable, axially aligned freeze-drying passage (34) and the second chamber (9) formed with at least one axially aligned transfer passage (36), at the rear ends in each case of the chambers (8, 9).

The method of the present invention comprising at least the following steps:

filling the second chamber (9) with a first drug component (14) of an injection solution (4), wherein the volume of the first drug component (14) is smaller than the volume of the second chamber (9);

inserting the second piston (7), which is compressed and allows the air to escape, into the first chamber (8) until it makes contact with an annular surface (18) in order to close the second chamber (9), the second chamber (9) containing a gas cushion (31);

filling the first chamber (8) above the second piston (7) with a solvent (19), for example water, or with the second drug component (15), inserting a first compressed piston (10) into the first chamber (8) and closing the first chamber (8), pushing in the first piston (10), with nozzle(s) (6) pointing upward in order to produce the injection solution (4) from the lyophilizate or the first drug component (14), and the solvent (19) or the second drug component (15) by means of a piston slide (20), wherein, by positive pressure in the first chamber (8), a second inner piston body (7.1) is pushed in a second outer piston ring (7.2) in the direction of a second chamber (9) until a previously closed transfer passage (16, 36) connects the second chamber (9) to the first chamber (8) and the solvent (19) or the second drug component (15) entirely enters the second chamber (9) and is dissolved or mixed with the lyophilizate or the first drug component (14) to provide the finished injection solution (4);

subsequently pushing in a first inner piston body (10.1) together with the second inner piston body (7.1) with the aid of the piston slide (20), by screwing the piston slide (20) into a thread, partial thread or latching element, and squeezing a gas bubble (31) out of the cylinder-piston unit (1), wherein the gas bubble (31) is displaced out of the second chamber (9) through (an) upwardly pointing nozzle bore(s) or outlet element(s) (6) and a membrane (26) which is fastened to the outer cylinder (13) or to the closure cap (11) and lifts off from the nozzle bore(s) or outlet element(s) (6) when the gas cushion (31) emerges, and closes the nozzle bore(s) or the outlet element(s) (6) again in a sterile manner (pressure control valve) after the gas cushion emerges.

The method of the present invention may also further comprise the step of freeze drying the first drug component (14) in the second chamber (9). The method of the present invention may also further comprise the step of checking the full emergence of the gas cushion (31).

LIST OF REFERENCE NUMBERS

1 Cylinder-piston unit
2 Cylinder
3 Chamber
4 Injection solution
5 End wall
6 Nozzle bore or outlet element
7 Second piston
7.1 Second inner piston body
7.2 Second outer piston ring
7.2a Quad ring
7.2b Slotted ring
8 First chamber
9 Second chamber
10 First piston
10.1 First inner piston body
10.2 First outer piston ring
11 Closure cap with latching element
12 Outer side of the pressure-stable outer cylinder 13
13 Outer cylinder, pressure-stable with latching groove
14 First component
15 Second component
16 Transfer passage, overflow passage, bypass, slot, combined, trifunctional
16.1 Freeze-drying passage, alternatively there is a slotted ring 7.2b in the second outer piston ring 7.2
16.2 Transfer passage, overflow passage, bifunctional
17 Lyophilizate
18 Annular surface
19 Solvent
20 Piston slide 21 Threaded flange
23 Threaded bore
24 Thread
25 Spring
26 Membrane on closure cap 11
27 Membrane alternatively on outer cylinder 13
28 Inner side of the chamber 9 or of the discharge funnel 30
29 Cone, truncated
30 Discharge funnel
31 Gas cushion, gas bubble
32 Retaining element
33 Spring hook
34 Freeze-drying passage
35 Cylinder wall
36 Transfer passage
37 Slot in outer cylinder 13
38 sealing lip

What is claimed is:

1. A method for filling a cylinder-piston unit (1) for a needle-free disposable injector, the cylinder-piston unit (1) for providing a sterile injection solution, the cylinder-piston unit (1) comprising a cylinder (2) having a cylinder wall (35), a chamber (3) which is arranged in the cylinder (2) and is intended for receiving an injection solution (4), and a second piston (7) arranged movably in the chamber (3), the chamber (3) of two-part design with a first chamber (8) and a concentric second chamber (9), the cross section of the first chamber (8) being larger than the cross section of the second chamber (9), a transition region of the cylinder (2) having an annular surface (18) between the first chamber (8) and the second chamber (9), the first chamber (8) formed such that it is closed by a first piston (10) having a first outer piston ring (10.2) in surrounding relationship with a first inner piston body (10.1), the first outer piston ring (10.2) in slidable relationship with the first chamber 8, the first inner piston body (10.1) in slidable relationship with respect to the first outer piston (10.2) and the second chamber (9) formed such that it is closed by the second piston (7), the first chamber (8) being separated from the second chamber (9), the second chamber (9) delimited by an end wall (5) of the cylinder (2) with at least one nozzle bore or outlet element (6), an outer cylinder (13) encasing the cylinder (2) proximate the second chamber (9), each nozzle bore or outlet element (6) configured to end in a truncated cone (29) on an outer side (12) of the outer cylinder (13), on the outer side (12) of the outer cylinder (13) a membrane (26) is stretched over each nozzle bore or outlet element (6), a closure cap (11) is connected directly or indirectly to a circumferential surface of the outer cylinder (13), and the second piston (7) having a second outer piston ring (7.2) in surrounding relationship with a second inner piston body (7.1), the second outer piston ring (7.2) in slidable relationship with respect to the first chamber (8), the second inner piston body (7.1) in slidable relationship with respect to the second outer piston ring (7.2) and the second chamber (9), and, wherein either the second outer piston ring (7.2) having at least one closable transfer passage (16) therein, the second inner piston body (7.1) maintaining each transfer passage (16) closed until a rear edge (21) of the second inner piston body (7.1) is pressed in the direction of the end wall (5) and reaches the transfer passage (16), or the cylinder wall (35) proximate the first chamber (8) having at least one closable, axially aligned freeze-drying passage (34) therein defined by an area of reduced wall thickness of the cylinder wall (35) and the cylinder wall (35) proximate the second chamber (9) having at least one axially aligned transfer passage (36) therein defined by an area of reduced wall thickness of the cylinder wall (35), the at least one closable, axially aligned freeze-drying passage (34) and the at least one closable, axially aligned transfer passage (36) at a respective rear end of the first chamber (8) and the second chamber (9), the second inner piston body (7.1) maintaining each axially aligned transfer passage (36) closed until a rear edge (21) of the second inner piston body (7.1) is pressed in the direction of the end wall (5) and reaches the axially aligned transfer passage (36), the method comprising at least the following steps:

filling the second chamber (9) with a lyophilizate or a first drug component (14) of an injection solution (4), wherein the volume of the first drug component (14) is smaller than the volume of the second chamber (9);

inserting the second piston (7), which is compressed and allows the air to escape, into the first chamber (8) until it makes contact with the annular surface (18) in order to close the second chamber (9), the second chamber (9) containing a gas cushion (31);

filling the first chamber (8) above the second piston (7) with a solvent (19), or with a second drug component (15), inserting the first piston (10), which is compressed, into the first chamber (8) and closing the first chamber (8), pushing in the first piston (10), with nozzle(s) (6) pointing upward in order to produce the injection solution (4) from the lyophilizate or the first drug component (14), and the solvent (19) or the second drug component (15) by means of a piston slide (20), wherein, by positive pressure in the first chamber (8), the second inner piston body (7.1) is pushed in the second outer piston ring (7.2) in the direction of the second chamber (9) until a previously closed transfer passage (16, 36) connects the second chamber (9) to the first chamber (8) and the solvent (19) or the second drug component (15) entirely enters the second chamber (9) and is dissolved or mixed with the lyophilizate or the first drug component (14) to provide the finished injection solution (4);

subsequently pushing in the first inner piston body (10.1) together with the second inner piston body (7.1) with the aid of the piston slide (20), by screwing a thread (24) of the piston slide (20) into a threaded bore (23) of a flange (22), and squeezing the gas cushion (31) out of the cylinder-piston unit (1), wherein the gas cushion (31) is displaced out of the second chamber (9) through the upwardly pointing nozzle bore(s) or outlet element(s) (6) and the stretched membrane (26) which is fastened to the outer cylinder (13) or to the closure cap (11) lifts off from the nozzle bore(s) or outlet element(s) (6) due to positive pressure in the second chamber (9) when the gas cushion (31) emerges, and the stretched membrane (26) functioning as a pressure control valve closes the nozzle bore(s) or the outlet element(s) (6) again in a sterile manner after the gas cushion emerges and there is no longer positive pressure in the second chamber (9).

2. The method as claimed in claim 1, further comprising the step of freeze drying the first drug component (14) in the second chamber (9).

3. The method as claimed in claim 1, further comprising the step of checking the full emergence of the gas cushion (31).

* * * * *